United States Patent [19]

Farhadieh et al.

[11] Patent Number: 5,164,189
[45] Date of Patent: Nov. 17, 1992

[54] SINGLE LAYER TRANSDERMAL DRUG ADMINISTRATION SYSTEM

[75] Inventors: Bahram Farhadieh, Libertyville; Rajeev D. Gokhale, Vernon Hills; Hana Berger, Lincolnshire, all of Ill.; Joseph Vallner, Mountainview, Calif.

[73] Assignee: G. D. Searle & Co., Chicago, Ill.

[21] Appl. No.: 667,992

[22] Filed: Mar. 11, 1991

Related U.S. Application Data

[63] Continuation-in-part of Ser. No. 425,766, Dec. 4, 1989, abandoned.

[51] Int. Cl.$^5$ .............................. A61F 13/00
[52] U.S. Cl. ............................ 424/448; 424/447; 424/449
[58] Field of Search ................ 424/449, 448, 447, 486

[56] References Cited

U.S. PATENT DOCUMENTS

| | | | |
|---|---|---|---|
| 3,797,494 | 3/1974 | Zaffaroni et al. | 424/449 |
| 3,935,329 | 1/1976 | Reilly et al. | 427/412.1 |
| 4,136,219 | 1/1979 | Odam et al. | 427/385.5 |
| 4,293,660 | 10/1981 | Sugio et al. | 525/68 |
| 4,360,618 | 11/1982 | Trementozzi | 524/141 |
| 4,433,088 | 2/1984 | Haaf et al. | 54/153 |
| 4,435,180 | 3/1984 | Leeper | 424/449 |
| 4,439,589 | 3/1984 | Alberts et al. | 526/209 |
| 4,440,906 | 4/1984 | Brandstetter et al. | 524/569 |
| 4,448,931 | 5/1984 | Sugio et al. | 525/68 |
| 4,513,120 | 4/1985 | Bennett et al. | 525/68 |
| 4,543,391 | 9/1985 | Kuribayashi et al. | 525/68 |
| 4,562,075 | 12/1985 | Ragadhyaksha | 514/788 |
| 4,578,423 | 3/1986 | Deets et al. | 525/68 |
| 4,605,670 | 8/1986 | Saito et al. | 514/619 |
| 4,627,852 | 12/1986 | Von Bittera et al. | 604/897 |
| 4,638,043 | 1/1987 | Szycher et al. | 528/75 |
| 4,661,104 | 4/1987 | Von Bittera et al. | 424/78 |
| 4,678,516 | 9/1987 | Alderman et al. | 106/197.1 |
| 4,695,465 | 9/1987 | Kisagawa | 424/449 |
| 4,699,777 | 10/1987 | Zupon et al. | 424/449 |
| 4,738,670 | 4/1988 | VonBittera et al. | 424/447 |
| 4,740,374 | 4/1988 | Nakano et al. | 424/448 |
| 4,746,509 | 5/1988 | Haggiage et al. | 424/449 |
| 4,758,434 | 7/1988 | Kydonieus et al. | 424/449 |
| 4,769,028 | 9/1988 | Hoffman et al. | 424/443 |
| 4,792,450 | 12/1988 | Kydonieus et al. | 424/449 |
| 4,906,169 | 3/1990 | Chien et al. | 424/445 |

FOREIGN PATENT DOCUMENTS

| | | |
|---|---|---|
| 0130839 | 1/1983 | European Pat. Off. |
| 0137545 | 4/1985 | European Pat. Off. |
| 0150021 | 7/1985 | European Pat. Off. |
| 2375295 | 7/1978 | France |
| 59-204650 | 11/1984 | Japan |

OTHER PUBLICATIONS

Tapash Ghosh et al., "Transdermal Drug Delivery Systems for a Model Beta Bocker: Levobunolol", Pharmaceutical Research, 7, 9, S-190 (1990).

R. Gokhale et al., "Bioavailability of a Transdermal Albuterol Patch", Pharmaceutical Research, 6, 9, S-167 (1989).

Tapash Ghosh et al., "Diffusion of Some Selected Beta-Blockers Across the Hairless Mouse Skin", Pharmaceutical Research, 3, 5, 52S (1986).

*Primary Examiner*—Thurman K. Page
*Assistant Examiner*—Leon R. Horne
*Attorney, Agent, or Firm*—Roberta L. Hastreiter; Paul D. Matukaitis

[57] ABSTRACT

A patch for the transdermal delivery of pharmaceutical drugs. The patch is characterized by having a single mass of elastomer in which the active drug and a percutaneous absorption enhancer are homogeneously dispersed throughout. The patch is especially well suited to delivering the beta$_2$ adrenergic agonist drug albuterol.

23 Claims, 5 Drawing Sheets

SINGLE LAYER TRANSDERMAL DRUG ADMINISTRATION SYSTEM

BACKGROUND OF THE INVENTION

This application is a continuation-in-part of application U.S. Ser. No. 425,766 filed on Dec. 4, 1989, entitled, "Novel Single Layer Transdermal Drug Administration System," now abandoned.

The present invention comprises a transdermal patch for the administration of drugs percutaneously. In particular, the invention is useful for the administration of the drug albuterol, a $\beta_2$ adrenergic agonist, which is useful, among other things, in the treatment of asthma by virtue of its action of inducing bronchodilation.

The practicality of administering a given drug percutaneously on a continuous basis depends upon the concentration of drug in the blood that is required to provide the desired pharmacologic effect, the degree to which the skin is permeable to the drug, and the amount of skin surface area that is available for drug administration.

The skin surface area which is available for drug administration, while theoretically being unlimited, is, for practical reasons, typically confined to a range of from about five square centimeters to about 100 square centimeters. With the available skin surface area fixed within this range, the matter then narrows as to whether sufficient drug will pass through that much skin surface area to provide the desired therapy. If it will, then it may not be difficult to effectively administer the drug percutaneously. If, however, the inherent permeability of the skin to the drug is so high or so low that too much or too little drug will pass through that area of skin, then the rate of administration of the drug to the skin must be controlled, or the permeability of the skin to the drug must be increased, as the case may be, to make percutaneous administration practical.

The present invention involves a drug delivery system in which the percutaneous administration of the active drug component is enhanced by the presence of a diffusion enhancer.

Systemically active drugs are conventionally administered either orally or by injection, with the primary objective of either mode being to achieve a given desired blood level of drug in circulation over a period of time.

These prior conventional methods of administering drugs to patients, however, possess certain shortcomings resulting in the failure to this goal.

The oral route of drug administration, for example, is inadequate for several reasons, even if the drug is administered to the patient at periodic intervals according to a well-defined schedule.

The rate of absorption of drug through the gastrointestinal tract is affected by both the contents in the tract and the passage of time as the drug travels through the small intestine. Therefore, such variables as whether the drug is administered before or after eating, and the type and quantity of food eaten, for example, high or low fat content, or whether the drug is administered before or after a bowel movement, affect the rate of absorption of the drug which takes place in the small intestine.

Additionally, the time of passage of drug through the small intestine is affected by the rate of peristaltic contraction, adding further uncertainty.

Also important is the rate of circulation of blood to the small intestine, and the fact that many drugs administered by this route are rendered inactive by gastric acid and digestive enzymes of the gastrointestinal tract or liver, where the drug can be metabolized to an inactive product.

These factors make it difficult to achieve a desired time course of concentration of drug in the blood.

The most widely-used dosage form of albuterol, an orally-administered, instant-release (IR) tablet, is administered to a patient every 6 hours. The controlled-release (CR) albuterol tablet is administered to a patient every 12 hours.

A significant disadvantage associated with the oral administration of albuterol is that orally-administered albuterol undergoes extensive first pass metabolism, probably in the gastrointestinal tract, with the result that the bioavailability of the drug formulation is reduced from a potential bioavailability of 100 percent to as low as 10 percent.

The most inevitable result of the oral administration of drugs through the gastrointestinal tract is that the level of drug in circulation surges to a peak level at the time the drug is administered, followed by a decline in drug concentration in the blood and body compartments. Thus, a plot of a drug in circulation versus time after the administration of several tablets of the drug per day will have the appearance of a series of peaks which may surpass the toxic threshold of the drug, and valleys which may fall below the critical point needed to achieve the desired pharmacologic or therapeutic effect of the drug, rather than a horizontal straight line indicating a steady-state concentration ($C_{ss}$) of the drug in circulation.

The administration of drugs by injection likewise entails certain disadvantages. For example, very strict asepsis must be maintained in order to avoid infection of the blood, the vascular system and the heart. Drug administration by poor intravenous injection technique may result in perivascular injection, when that was not intended. The typical result of injection of a drug into the blood is a sudden rise in the blood concentration of the drug followed by an uncontrollable decline in drug concentration. Additionally, administration of drugs by injection is inconvenient and painful.

Other dosage forms for systemic administration of drugs, such as rectal suppositories and sublingual lozenges, also produce non-uniform levels of the therapeutic agent in circulation. These dosage forms require great patient cooperation and have low patient acceptability, resulting in decreased patient compliance with a prescribed drug regimen, which is the most common failure of drug therapy.

To avoid the problems discussed above, a new branch of drug delivery has developed in which systemically-active drugs are administered through the skin or mucosa of a patient. Uncertainties of administration through the gastrointestinal tract, and the inconvenience of administration by injection, are decreased or eliminated by this system of drug administration. The ease of application, and simplicity of removal, of such a drug delivery system produces a desirable psychological effect on the patient. This means better patient cooperation, resulting in more effective therapy. Because a high concentration of drug never enters the body, problems with pulse entry (varying levels of drug in the patient's circulation, depending upon the time of drug administration) are overcome.

Despite these advantages of administering systemically-active drugs through the skin, many problems exist with prior art devices designed for this purpose. Many such devices do not provide a continuous administration of drug to the patient, or a continuous delivery rate. Also, many such devices are irritating to the patient's skin or mucosa and/or have limited application to a relatively narrow group of therapeutic drugs. Frequently, new application systems must be designed for drugs which are incompatible with prior art application systems.

The release of a drug from a topical preparation can be materially affected by the vehicle in which it is applied. Correct formulation of a topical agent will ensure that it exerts its maximal activity, while an incorrect formulation of the agent may reduce its activity, or even render a potent drug essentially ineffective.

The primary requirement for topical drug therapy is that a drug incorporated in a vehicle reach the skin surface at an adequate rate and in sufficient amounts. The drugs must then penetrate the outer horny layer of the skin.

Drug penetration through the skin depends upon release of the drug from the topical delivery device and transport of the drug across the skin barrier. In most cases, the rate-limiting step is skin transport. However, formulation changes can affect both of these steps.

Transport of drug substances through the skin is affected by a variety of factors. For diffusion to occur, the drug must be in solution. Thus, solubility of the drug in the fluids in and around the epidermal cells is of great significance.

The polarity of the drug molecules must also be considered. When hydrated, the stratum corneum contains approximately 75% water, 20% protein and 5% lipid. During hydration, water accumulates near the outer surface of the protein filaments. Polar molecules are believed to pass through this aqueous layer, while nonpolar molecules probably dissolve in, and between, the protein filaments.

The oil-water partition coefficient is also important. If a substance is more soluble in the stratum corneum than in the vehicle in which it is dissolved, then transfer to the former will be favored. In vitro and in vivo studies support the postulate that the release of a drug will be facilitated by using vehicles having a low affinity for the penetrant. Thus, in formulation, care is necessary to ensure that the benefits of drug solubility in relation to skin penetration are not reduced by the use of excipients which have too high an affinity for the drug.

A further factor which has been shown to influence drug effectiveness, and which can be manipulated by the formulator, is the level of hydration of the stratum corneum. Hydration results from water diffusing from underlying epidermal layers or from perspiration that accumulates under an occlusive vehicle. In general, increasing the moisture content of the stratum corneum increases the rate of passage of all substances which penetrate the skin.

Researchers working in the art have conducted studies of the effects of vehicles containing substances which materially affect skin penetration. A range of agents has been recorded as having accelerant action, in particular propylene glycol, surface active agents, dimethylsulfoxide, and dimethylacetamide. These substances, however, have certain drawbacks, including skin irritation potential. Their use to date has been limited.

B. Idson, *Cosmetics and Toiletries* 95, 59 (1980), has concluded that the factors affecting drug penetration into the skin and, consequently, in most cases effectiveness, are complex. The vehicle that provides ideal conditions for one drug may prove unsatisfactory for another.

The present invention seeks to overcome prior problems with the continuous administration of a drug to a patient, and with the delivery rate of the drug in general, and has been found to work particularly well with adrenergic agonists, and especially well with albuterol, a selective $\beta_2$ adrenergic agonist.

Another object of this invention is to provide a device for the administration of albuterol to a patient in a reliable and easily-applied device for continuously administering the drug to the patient in controlled quantities through the patient's intact skin or mucosa.

Another object of this invention is to provide for such a drug delivery device which will cause little, if any, dermal or mucosal irritation to the patient.

Another object of this invention is to provide a drug delivery device which will be especially useful and acceptable in pediatric patients and geriatric patients.

A further object of this invention is to provide for a unitary, non-lamellar, single-layered drug delivery device.

Yet another object of this invention is to provide a drug administration device which will provide a continuous dosing of the drug to the patient over a 24-hour period.

The transdermal drug administration patches of the present invention generally provide a continuous administration of drug to the patient. In addition, these patches generally cause little or no dermal or mucosal irritation to the patient. Both of these qualities are significant advantages of the patches of the present invention in comparison with many of the transdermal drug administration systems known in the art. Many of the prior art devices designed to deliver systemically active drugs through the skin or mucosa of a patient fail to provide a continuous administration of the drug to the patient, and/or do not provide a continuous delivery rate of the drug to the patient. Even if a transdermal patch does administer a particular drug appropriately through the skin or mucosa of a patient, the patch will not be a desirable form of administration for the drug if the patch is irritating to the patient's skin or mucosa.

Prior to the invention of the transdermal albuterol patches described herein, researchers working in the field were unable to successfully deliver albuterol to a patient by means of a transdermal patch.

The transdermal albuterol patches of the present invention feature, in addition to the benefits already described above, a 100% skin bioavailability of drug to a patient, a good margin of safety in pediatric and geriatric patients and ease of administration.

Albuterol administered transdermally through a patch of the invention is useful for actual asthma therapy, rather than merely for prophylaxis. It is also useful in both pediatric age groups and geriatric populations, both of which require simple-to-administer regimens that do not rely on the responsibility or memory of the patient to comply with several daily dosage administrations of the drug, as is often needed with conventional tablets or capsules of albuterol. Transdermal albuterol therapy would also be useful after the treatment of an acute asthma attack to prevent the exacerbation of such an attack. Clinically, it would also be useful either as a substitute for intravenous therapy or as an improvement over oral therapy.

In addition to being convenient, transdermal albuterol therapy has a significant margin of safety. Significantly, an on-going therapy, such as with sustained-release oral formulations, could be interrupted if the average plasma level of the drug were too high. Once the patient was stabilized at a lower plasma level of drug, the transdermal albuterol patch would be beneficial to maintain consistent plasma levels of albuterol at a more desirable lower level.

Additionally, albuterol can be used transdermally as a tocolytic (obstetric) agent. Preterm labor occurs in approximately 10% of pregnancies. Commonly, beta-mimetic agents are employed for preterm labor. Albuterol is currently used for preterm labor, with the plasma albuterol levels needed for uterine relaxation being 8 to 33 nanograms of drug per milliliter. Such levels are within the range of albuterol delivered by the transdermal albuterol patches of the present invention.

The albuterol patches of the present invention also have the potential advantage of safety over the intravenous route of drug administration, and the further advantage of a more uniform dosing of the drug to the patient in comparison with the oral route of drug administration, during the sensitive and critical period during which labor occurs. Such a use of an albuterol patch of the invention may be adjunctive with bed rest and intravenous and oral agents, or may be primary therapy as a substitution for intravenous beta-mimetic agents.

Additionally, a transdermal albuterol patch of the invention may find usage as an emergency therapy for the treatment of urticaria (hives).

The usefulness of albuterol as a bronchodilator is not limited to the treatment of asthma. Albuterol can also be used as a bronchodilator in the treatment of bronchitis, chronic obstructive pulmonary disease and other obstructive pulmonary diseases.

● —Represents a single-layer albuterol transdermal patch (Example 2) (n=3).

▣ —Represents a double-layer albuterol transdermal patch (Example 3) (n=6).

Figure 4:
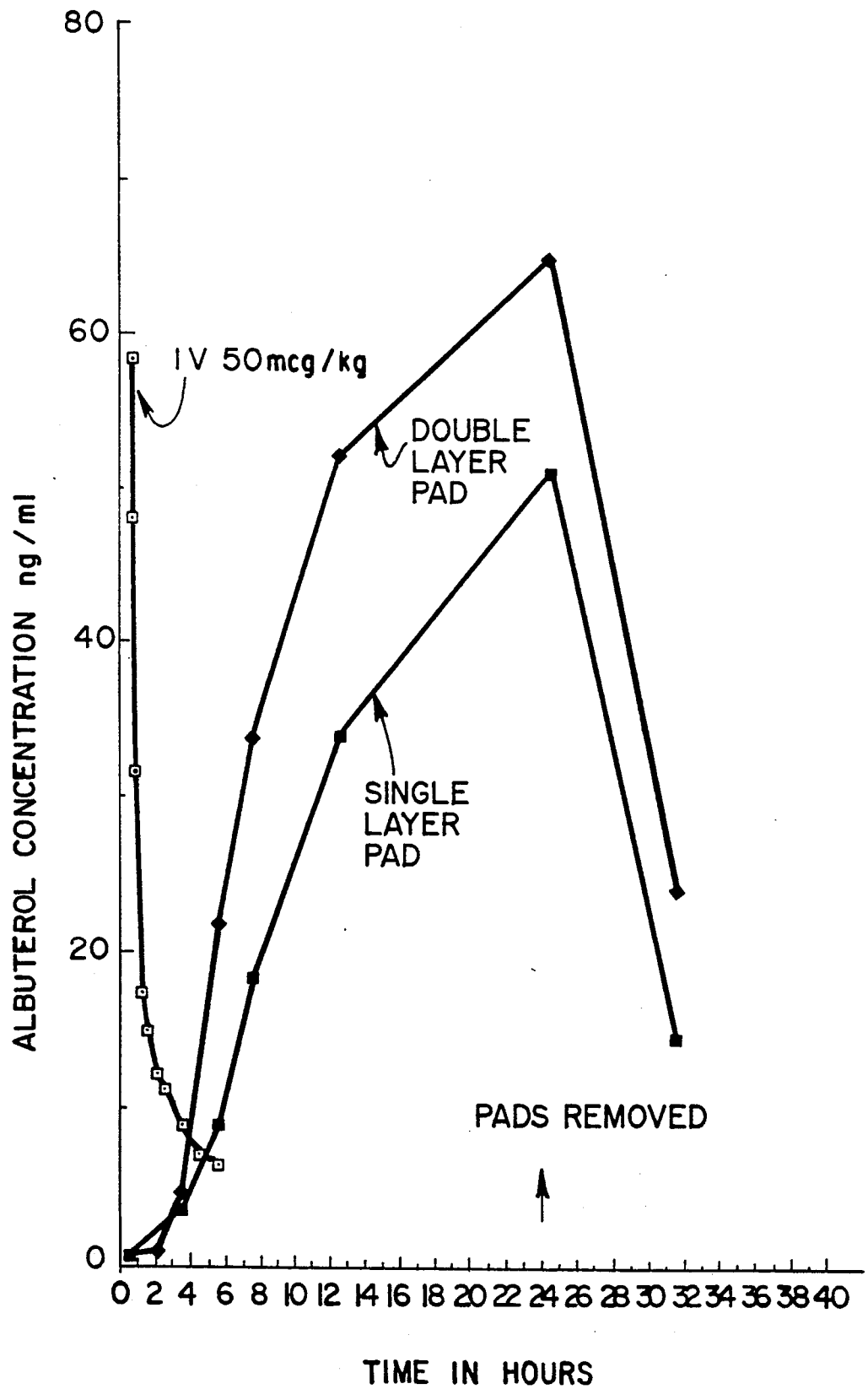

FIG. 4 is a plot of serum albuterol concentrations versus time following the intravenous (n=4) (▣) (Example 1(d)), and single-layer (n=4) (■) and double-layer (n=3) (●) transdermal patch (Example I(e)) ad-ministration of albuterol in Rhesus monkeys. The error bars represent the standard deviation of the mean.

Figure 5:
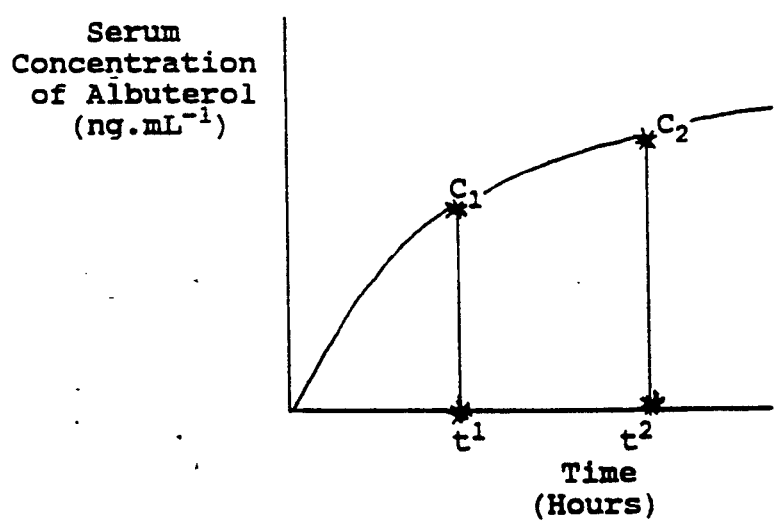

FIG. 5 shows how "Area under the curve" (AUC) values [values of the amount of albuterol int eh serum at a given point in time (ng.mL$^{-1}$.hours)] were calculated using the standard trapezoidal rule and the following mathematical formula, as described by M. Gibaldi et al. at Page 447:

$$\text{Area Under the Curve (AUC)} = \frac{(C_1 + C_2)}{2} \times (t_2 - t_1)$$

where $C_1$ represents the first concentration, $C_2$ represents the second concentration, $T_1$ represents the first time and $t_2$

SUMMARY OF THE INVENTION

The present invention comprises a transdermal patch for the administration of drugs percutaneously.

The most preferred embodiment of this invention is a non-laminated monolayer patch for the transdermal administration of a drug to a patient comprising an elastomeric matrix material of predetermined thickness and area; an active drug ingredient dispersed throughout the matrix; and a diffusion enhancer dispersed throughout the matrix.

Additionally, a suitable plasticizer and/or a solubilizing agent for the active ingredient can conveniently be incorporated into the patch.

Elastomeric Matrix Materials

Suitable elastomeric matrix materials for use in the patches of the invention comprise the following polymers:

Polyethylene,
Polypropylene,
Polyethylene terephthalate,
Polyvinylidene fluoride,
Polymethyl methacrylate,
Polyurethane-polyamide copolymers,
Poly(2-hydroxyethyl methacrylate) (HEMA-hydrogel),
Polyalkyl acrylate esters (bioadhesive polymers),
Polyisobutylene (bioadhesive polymer),
Polydimethylsilicone with resin (bioadhesive polymer), and
Silicone elastomers.

The patches of the present invention preferably utilize a silicone elastomer as the matrix. Silicone elastomers have alternating silicon and oxygen atoms for a backbone. Double bonds are generally absent in such a backbone and, therefore, the numerous forms of stereoisomers ordinarily found in unsaturated hydrocarbon rubbers do not have counterparts in the silicone rubbers. An especially useful silicone elastomer for use in the patches of the invention is Silastomer ™ X7-3058, available from Dow Corning, Inc., Midland, Mich.

Generally, when an amine or an alcohol, such as albuterol or n-dodecanol, respectively, is incorporated into certain elastomeric matrix materials, such as silicone matrix materials, the alcohol will have an undesirable effect on the cure of such materials, that is, the effect of preventing the elastomeric matrix materials from becoming or remaining hardened. Thus, the elastomeric matrix materials would be expected to have a sticky consistency, or a consistency like that of a petroleum jelly, and, thus, would not be suitable for use in a transdermal drug administration patch. Consequently, it was surprising and unexpected when elastomeric matrix materials were discovered which would become hardened, and remain in a suitably-hardened state, when albuterol and/or various alcohol diffusion enhancers, such as n-dodecanol, were dispersed therein.

In the most preferred embodiment of the present invention, the active drug ingredient is albuterol, most preferably as the free base.

Diffusion Enhancers

Diffusion enhancers for use in the patches of the invention are suitably chosen from the group comprising:
Decymethyl Sulphoxide,
Hexylmethyl Sulphoxide,
Trimethyl phosphine oxide,
N,N-Dimethyl-m-toluamide,
Tetrahydrofuryl alcohol,
Dimethyl acetamide,
Propylene glycol,
n-methyl-2-pyrrolidone,
2-pyrolidone,
1-ethyl-2-pyrolidone,
Sodium lauryl phosphate,
Triethanol amine lauryl phosphate,
Poloxamer 231,
Polyoxyethylene 4 lauryl ether,
Poloxamer 182,
Urea,
Isopropyl myristate,
Isopropyl palmitate,
Butyrolactone,
Vanillin,
Stearyl alcohol, and the normal hydrocarbon alcohols.

Preferred diffusion enhancers for use in the patches of the invention are normal hydrocarbon alcohols, with the most preferable diffusion enhancer being n-dodecanol, dispersed throughout the elastomeric matrix.

DETAILED DESCRIPTION OF THE INVENTION

Permeation of Drug through the Matrix Material

The present invention comprises a transdermal patch which is suitable, by virtue of the rate-controlling materials employed therein, for the predetermined controlled administration of drug to the skin or mucosa of a mammal over a period of time. The patch of the invention is applied to the patient's skin or mucosa and should be in firm contact therewith so as to form a tight seal. Flow of drug from the patch to the patient's skin or mucosa is metered through the matrix material of the patch in accordance with the laws of diffusion, as hereinafter discussed, at a predetermined rate. In operation, drug molecules are continuously removed from the patch, migrating through the patch to the skin or mucosa of the patient, where the drug is absorbed and enters the patient's circulation through the capillary network.

The rate of passage or permeation of drug through the elastomeric matrix material of the patch is determined by the diffusive flux of the drug molecules through the material, as is the case where the material is of a solid nature in which the drug molecules can dissolve in, and flow through, to a direction of lower chemical potential.

The release rate of the drug can be controlled in accordance with "Fick's First Law," depending on the design of the particular drug transfer mechanism, which may vary according to certain variables, such as the diffusivity and solubility of the drug being employed in the diffusive medium, and the thickness of the matrix material of the patch.

The mechanism of action of the diffusion enhancers described herein may be to increase the diffusivity of active ingredient through the patch matrix material. This mechanism of action shall be understood to attach to the term "diffusion enhancer" as used herein.

Elastomeric Matrix Materials

Preferred elastomeric matrix materials for use in the patches of the invention are the organopolysiloxane rubbers, commonly known as silicone rubbers. Suitable silicone rubbers are the conventional heat vulcanizable (curable) silicone rubbers and the room temperature vulcanizable silicone rubbers. Room temperature vulcanizable silicone rubbers will require the use of a curing agent or catalyst. The most especially preferred silicone rubber for use in the patches of the invention is Silastomer TM X7-3058, available from Dow Corning, Inc. Other room temperature vulcanizable silicone rubbers suitable for use in the patches of the invention are also commercially available.

A typical catalyst that will cure silicone rubber at room temperature is stannous 2-ethyl hexoate, which can be present in a range of from about 0.0625% to about 0.5%.

Exemplary patents disclosing the preparation of silicone rubbers are U.S. patent Nos. 2,541,137; 2,723,966; 2,863,846; 2,890,188; 2,927,907; 3,002,951 and 3,035,016.

Elastomer can be present in the patches of the invention in an amount ranging from about 25 to about 95 per cent, weight to weight. More preferably, it can be present in an amount ranging from about 65 to about 90 per cent, weight to weight.

Catalysts

Catalysts which may be employed to cure the elastomeric matrix material component of the patches of the invention include stannous 2-ethyl hexoate and Dow X7-3075 catalyst (Dow Corning, Inc.).

Catalyst can be present in the patches in a range of from about 0.0625% to about 0.5%, preferably in a range of from about 0.125% to about 0.25%.

Patch Thickness and Area

The thickness of the transdermal patches of the invention can be manipulated, as described in Examples 2 and 3 below, by any conventional film casting apparatus, or other suitable apparatus. Although the thickness of the patches may vary between about 0.05 and about 0.5 millimeters, the preferred range of thickness is between about 0.20 and about 0.40 millimeters.

The area of the patches of the invention may also vary, and may be in the range of from about 1 to about 100 square centimeters, preferably from about 4 to about 16 square centimeters. The patches, which are generally light yellow in color, may be square, circular, rectangular or triangular in shape, or may be of other shapes. The patches may be cut to an appropriate size and shape with any sharp instrument, such as a razor blade.

Diffusion Enhancers

A diffusion enhancer is employed in the patches of the present invention, with the most preferred diffusion enhancers being the normal hydrocarbon alcohols of one to twenty carbon atoms. As the chain length of the alcohol increases, the effectiveness of the diffusion enhancer generally increases up to a point. The most preferred diffusion enhancer for use in the patches of the invention is n-dodecanol. n-dodecanol can be present in an amount ranging from about 3 to about 30 per cent, weight to weight. More preferably, it can be present in an amount ranging from about 6 to about 15 per cent, weight to weight.

Plasticizers

Plasticizers are useful for increasing the plasticity of polymers. In a preferred embodiment of the patches of the present invention, a suitable plasticizer is employed. Preferred plasticizers include diols, triols, and other polyols. The most preferred plasticizer is glycerol.

Solubilizing Agents

In a preferred embodiment of the patches of the present invention, a solubilizing agent for the active ingredient is employed. Preferred solubilizing agents include the normal hydrocarbon alcohols, with n-hexanol being the most preferred solubilizing agent. n-hexanol can also act as a useful plasticizer.

Active Agents

The most preferred patch of the present invention comprises, out of 100%, Dow Silastomer ™ X7-3058:Dow X7-3059 crosslinking agent (97.86:2.14), 71.81%, w/w; albuterol, 15.98%, w/w; n-dodecanol, 9.99%, w/w; glycerol, 1.75%, w/w; and hexanol, 0.35%, w/w; with a suitable organotin catalyst, 0.125%, w/w (generally stannous 2-ethyl hexoate).

All materials used in the patches of the present invention are dispersed uniformly throughout the matrix material employed therein. This dispersion results from the use of an elastomeric matrix material.

The amount of active agent incorporated within the elastomeric matrix material of the patches of the invention to obtain the desired therapeutic effect will vary depending upon the desired dosage of the active agent, the length of time the patch is to remain on the skin or the body mucosa of the patient and the area and thickness of the patch. Patient serum concentrations of the active agent can thus be adjusted by varying the concentration of the active agent in the patch, the length of time the patch is to remain on the skin or body mucosa of the patient or the patch size.

Because the patches of this invention are designed to control drug administration for an extended period of time, ideally 24 hours or more, absent toxicity concerns, there is no critical upper limit on the amount of active agent incorporated into the patches. The lower limit of the amount of active agent incorporated into the patches is determined by the fact that sufficient amounts of the agent must remain in the patches to maintain the desired dosage of the agent for the particular patient being treated.

In order to achieve a therapeutic effect of albuterol in a human adult suffering from a condition which is treatable with albuterol, the patient serum concentration of albuterol should be in the range of between about 2 and about 33 nanograms of albuterol per milliliter of serum, and most preferably between about 4 and about 8 nanograms per milliliter. From about 4 to about 8 nanograms of albuterol per milliliter is desirable for treating bronchoconstriction, and from about 8 to about 33 nanograms of albuterol per milliliter is desirable for using albuterol as a tocolytic agent.

The effective rate of release of the active agent from the patches of the invention to the skin or mucosa of a patient can be in the range of from about 0.2 to about 2.0 milligrams of active agent per square centimeter of skin or mucosa per day ($mg.cm^{-2}.day^{-1}$). A more preferred range would be from about 0.3 to about 0.85 milligrams of active agent per square centimeter of skin or mucosa per day. The exact amount will depend on the desired dosage of the active agent, as well as the condition being treated.

Those skilled in the art can readily determine the rate of permeation of active drug ingredient through a particular matrix material, and through selected combinations of matrix materials, to be employed in a patch of the invention. Standard techniques employed for making such determinations are described in the Encyclopedia of Polymer Science and Technology, Volumes 5 and 9, Pages 65 to 85 and 795 to 807 (1968), and the references cited therein, the disclosures of which are incorporated herein by reference.

Albuterol (nonmicronized or micronized) can be present in the patches of the invention in an amount ranging from about 2 to about 30 per cent, weight to weight. More preferably, it can be present in an amount ranging from about 8 to about 24 per cent, weight to weight, and most preferably, in an amount ranging from about 12 to about 20 per cent, weight to weight.

Both nonmicronized and micronized albuterol may be employed in making the transdermal patches of the invention. Both types of albuterol work well, and neither type is preferable over the other. However, it may be easier to obtain micronized albuterol.

Backing Members

Various occlusive and non-occlusive, flexible and non-flexible backing members can be used in the patches of the present invention, if desired.

Suitable backing members for use in the patches of the invention include cellophane, cellulose acetate, ethylcellulose, plasticized vinylacetate-vinylchloride copolymers, polyethylene terephthalate, nylon, polyethylene, polypropylene, polyvinylidenechloride, paper, cloth, foam and aluminum foil.

Protective Release Films and Foils

To prevent the passage of drug away from the exposed surface of a patch of the invention prior to its use, the surface of the patch generally can be covered with a protective release film or foil, such as waxed paper.

To enhance the stability of the active compound(s) employed in a patch of the invention, the patch is usually packaged between hermetically-sealed polyethylene terephthalate films or aluminum foils under an inert atmosphere, such as gaseous nitrogen.

Application of Patches

The patches of the invention are applied to the skin of patients. A patch should be in firm contact with the patient's skin, preferably forming a tight seal therewith. Drug within the patch will then migrate through the patch to the patient's skin by diffusion. When drug is in contact with the patient's skin, drug molecules which are continuously being removed from the outer surface of the patch migrate through, and are absorbed by, the skin, entering the patient's circulation through the capillary network. The patch can be applied to any area of the patient's skin, including the oral mucosa, for example, by application of the patch to the patient's palate or buccal mucosa. In addition, the patches of the invention can be used to administer drugs to other mucosa of the body, for example, by application to the vaginal mucosa, the rectal mucosa, etc.

Patch Handling and Storage

The transdermal patches of the invention should be stored at controlled room temperature, and should be protected from light. Patches stored under cold conditions tend to show crystallization on the surface. This is not observed for patches stored at room temperature.

In order for an operator who is administering a transdermal patch of the invention to a patient (physician, nurse, etc.) to avoid unwanted exposure to an active drug ingredient dispersed throughout the matrix of the patch, gloves should be worn when handling the patch, and direct contact between the patch and the operator's skin should be avoided.

While the various aspects of the transdermal patches of the present invention are described herein with some particularity, those of skill in the art will recognize numerous modifications and variations which remain within the spirit of the invention. These modifications and variations are within the scope of the invention as described and claimed herein.

EXAMPLES

The examples presented below describe and illustrate the methods for the preparation of the transdermal patches of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the transdermal patches of the present invention.

All patents and publications referred to in the examples, and throughout the specification, are hereby incorporated herein by reference, without admission that such is prior art.

In the examples presented below, both single-layer (Examples 2 and 4) and double-layer (Example 3) albuterol patches of the invention designed for once-a-day application were prepared.

In vitro and in vivo experiments were then conducted (Example I) with both the single-layer and double-layer albuterol patches of the present invention, prepared as described in Examples 2 and 3, respectively, or prepared as otherwise described.

In the preliminary in vitro experiments (Examples 1(a), 1(b) and 1(c)), the in vitro drug release of single-layer (Example 2) and double-layer (Example 3) transdermal patch formulations of the invention were monitored via the permeation of albuterol from the patches through hairless mouse skin (Example 1(a)) and monkey skin (Example 1(c)), and via the dissolution of albuterol from the patches in water (Example 1(b)).

The in vivo albuterol absorption, bioavailability, pharmacokinetics and skin irritation were then monitored in Rhesus monkeys (Examples 1(e) and 1(f)). Intravenous albuterol pharmacokinetics was also followed using a "crossover design" (a study in which the same animals are used for each of the different in vivo experiments performed, such as for the application of single-layer transdermal albuterol patches, the application of double-layer transdermal albuterol patches, and the intravenous administration of an albuterol aqueous solution) in the same monkeys (Examples 1(d) and 1(f)).

In these in vivo experiments, at different times, single-layer and double-layer albuterol patches of the invention, prepared as described in Examples 2 and 3, respectively, were separately applied to the chest area of four female Rhesus monkeys, designated #388, #391, #423 and #430, and an albuterol aqueous solution was separately injected into the saphenous vein of the same monkeys at another time, in a "crossover design." Blood samples from the monkeys were withdrawn at regular intervals after albuterol patch application or injection and analyzed by an HPLC method. Skin irritation of the monkeys was also measured by a Draize Score Test.

Further in vivo skin irritation and sensitization tests were then conducted with rabbits (Example 1(g)) and guinea pigs (Example 1(h)), respectively.

Finally, in vitro stability studies were conducted to study the degradation of the transdermal albuterol patches of the invention over time (Example 1(i)).

Each of the experiments described in examples 1(a)-(f) was conducted several times with both single-layer and double-layer transdermal albuterol patches of the invention. The number of times a particular experiment was conducted is indicated in each example. For example, (n=3) means that a particular experiment was conducted three times.

Materials and Animals

Chemicals and solvents used in the experiments were obtained from the following sources: nonmicronized albuterol from Co. Pharmaceutica, Milanese, Italy; micronized albuterol from Labochim, Milano, Italy; methanol, acetonitrile and chloroform from Burdick Jackson, Muskegon, Mich.; water from Fisher Scientific Company, Fairlawn, N.J.; Di (2-ethylhexyl) phosphate (DEHP), sodium phosphate monobasic, sodium phosphate dibasic, bamethane sulfate, glycerol, n-hexanol and n-dodecanol from Sigma Chemical Company, St. Louis, Mo.; 1-pentane sulfonic acid sodium salt from Kodak, Rochester, N.Y.; 0.9% sodium chloride irrigation solution from Travenol Laboratories, Deerfield, Ill.; Silastomer TM X7-3058 elastomeric matrix material, X7-3059 crosslinking agent and X7-3075 catalyst from Dow Corning, Inc., Midland, Mich.; and triethylamine from Aldrich Chemical Company, Inc., Milwaukee, Wis.

All solvents and chemicals were ACS analytical grade or HPLC grade.

While nonmicronized albuterol was employed in Examples 1(a)-(f), 2 and 3, micronized albuterol was used in all of the other examples.

The four female Rhesus monkeys used in the experiments described hereinbelow (#388, #391, #423 and #430) were Macaca Mulata monkeys which were obtained from the University of Texas in Austin, Tex.

Generally, the computer programs referred to in the examples merely provide a simpler and quicker means for obtaining the answers to the mathematical equations specified or referred to therein.

SUMMARY OF EXAMPLES, TABLES AND FIGURES

Figure 1:
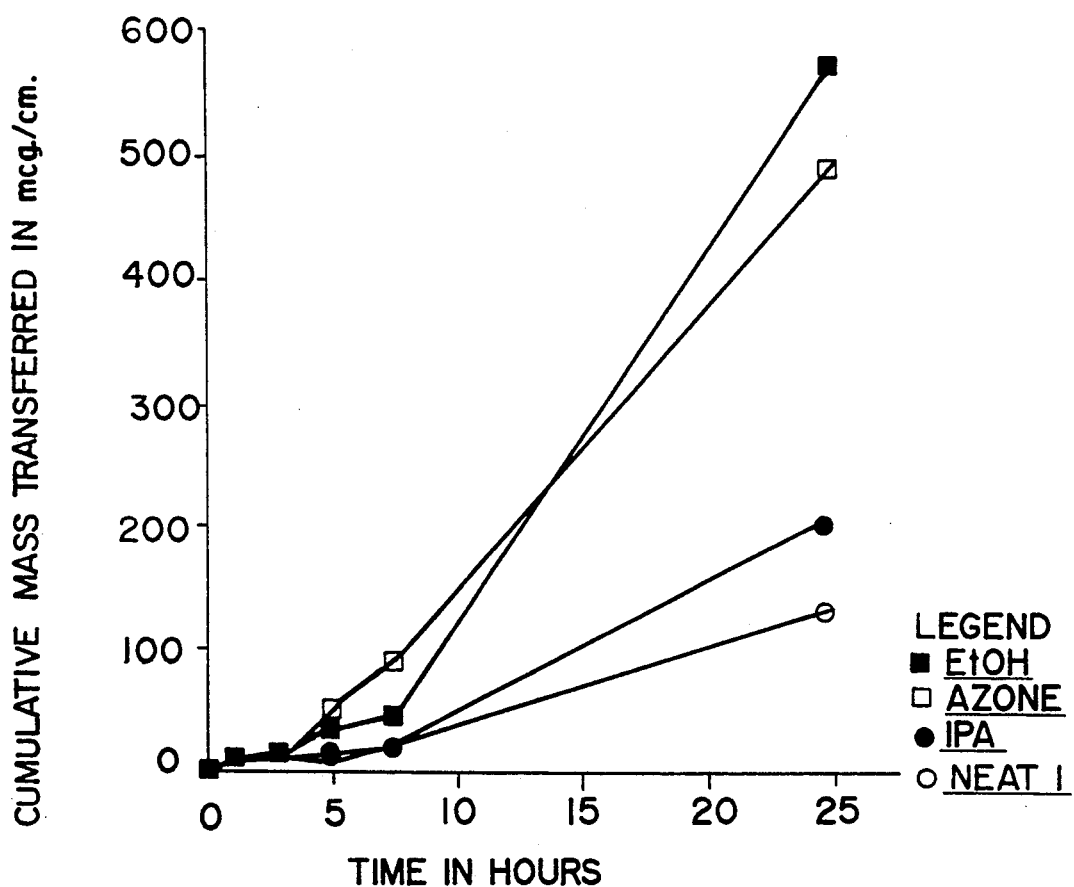
FIG. 1 is a plot of the in vitro transfer of albuterol transdermally through the skin of a hairless mouse contained in a Franz Diffusion Cell Assembly (Example 1(a) versus time, showing how various adjuvant agents affect the flux of albuterol through the mouse skin. It can be seen that ethanol was the most effective agent when compared with prior art agents, such as Azone and isopropyl alcohol (IPA).
Figure 2:
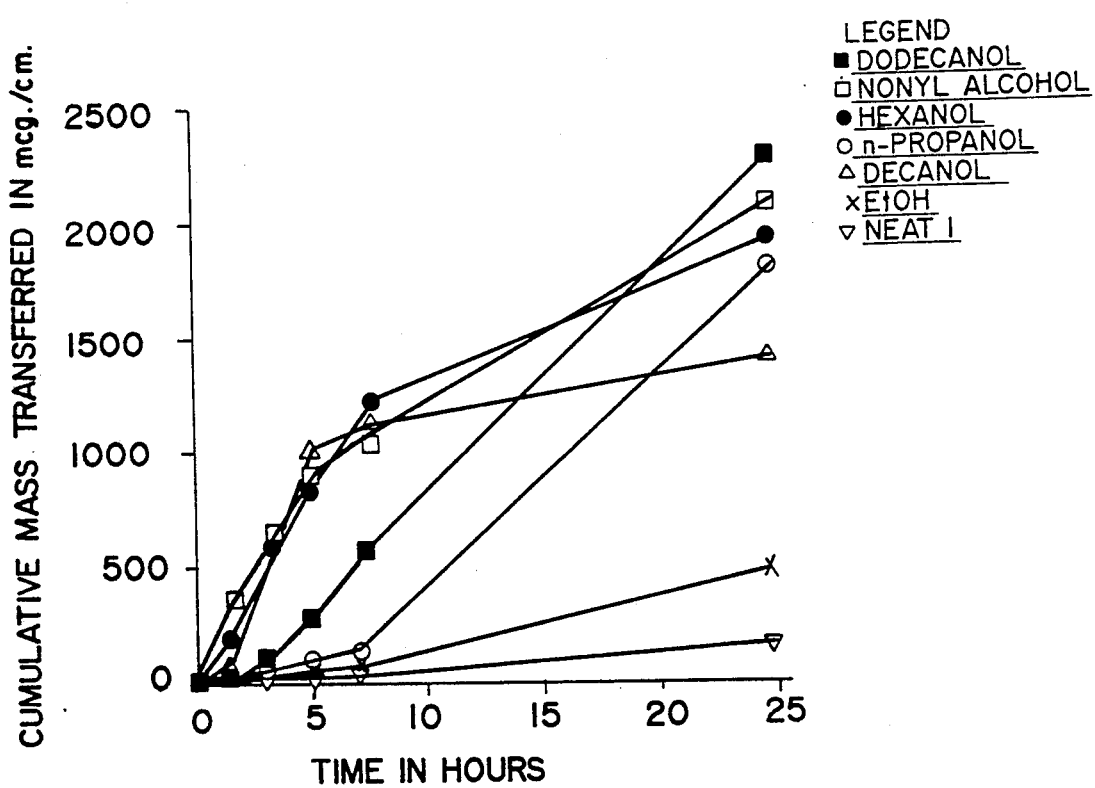
FIG. 2 is the same type of plot as FIG. 1, except that the agents tested are normal hydrocarbon alcohols. It can be seen that, in general, agent effect on albuterol flux increases as the chain length of the alcohol increases.
Figure 3:
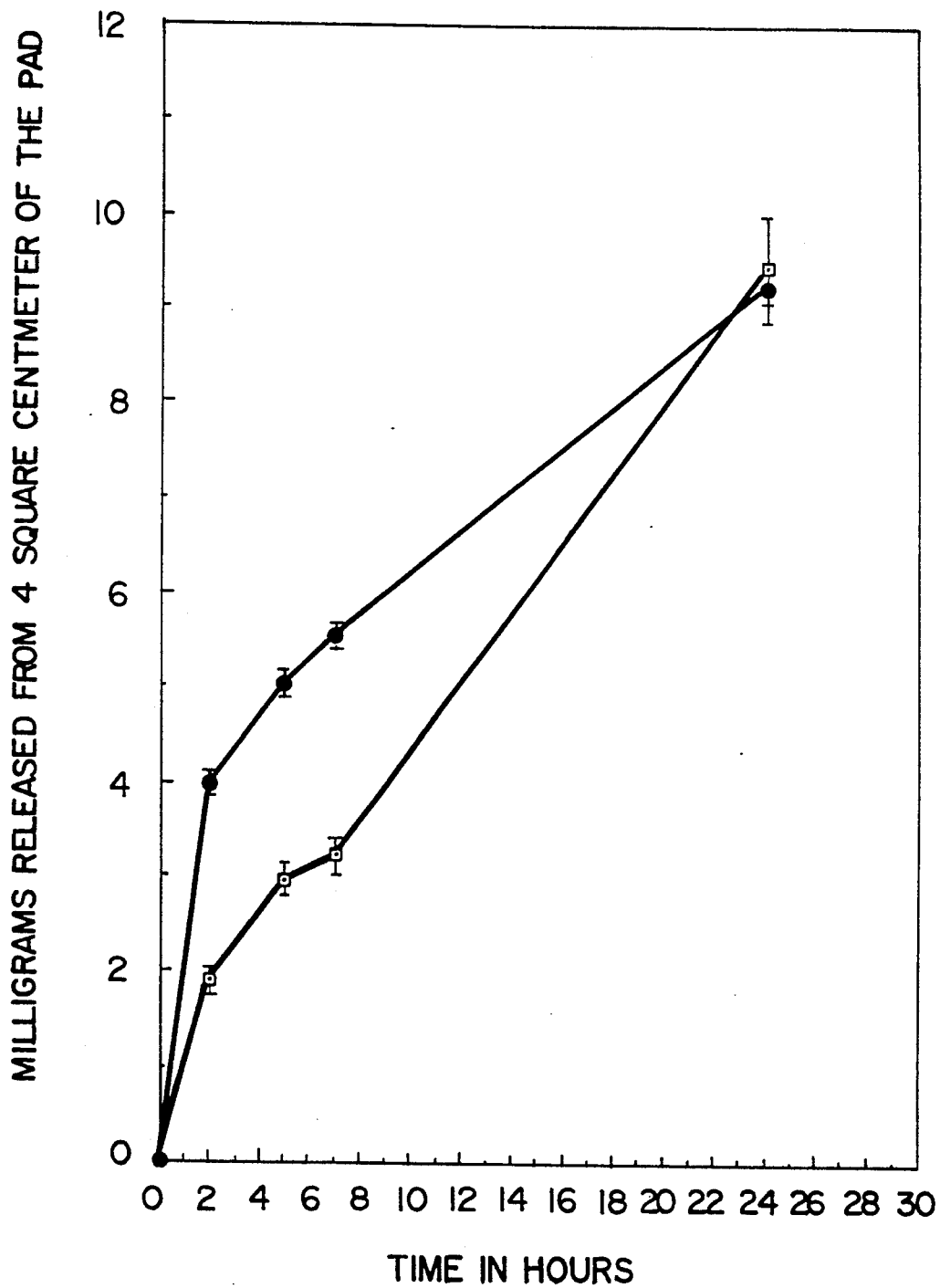
FIG. 3 is a plot of albuterol concentrations versus time following albuterol transdermal patch dissolution in a Hanson's Dissolution Test Apparatus (Example I(b)) showing the in vitro release of albuterol from the patches. The error bars represent the standard deviation of the mean.

The examples, tables and figures which correspond to the various experiments described in the examples are as follows:

| Subject Matter | Corresponding Example(s) | Corresponding Table(s) | Corresponding FIG(S). |
|---|---|---|---|
| (1) Franz Cell Experiments | Example 1(a) | Table I | FIGS. 1 and 2 |
| (2) Dissolution Experiments | Example 1(b) | Table II | FIG. 3 |
| (3) Residue Analysis Experiments | Example 1(c) | Table III | None |
| (4) Intravenous Administration of Albuterol | Example 1(d) and (f) | Tables IV and VI | FIG. 4 |
| (5) Patch Administration of Albuterol | Examples 1(e) and (f) | Tables III, V, VII, XI and XII | FIG. 4 |
| (6) Comparison of In Vitro Patch Parameters | Examples 1(a), (b) and (c) | Tables I, II, III and IX | None |
| (7) Rhesus Monkey In Vitro-In Vivo Data Comparison | Examples 1(c), (d) and (f) | Tables VII and VIII | None |
| (8) Hypothetical Human Serum Albuterol Concentrations | Example 1(f) | Tables X and XI | None |
| (9) Rabbit Skin Irritation Experiments | Example 1(g) | Tables XIII, XIV and XV | None |
| (10) Guinea Pig Skin Sensitization Experiments | Example 1(h) | Tables XVI, XVII and XVIII | None |
| (11) Patch Stability Studies | Example 1(i) | Tables XIX, XX and XXI | None |

EXAMPLE 1

Example 1(a)

In Vitro Franz Cell Experiments (1) Albuterol Transdermal Patches

In these preliminary in vitro experiments, the in vitro albuterol release of single-layer (Example 2) and double-layer (Example 3) transdermal patch formulations of the invention were monitored via the permeation of albuterol from the patches through hairless mouse skin to determine whether or not albuterol would pass through the mouse skin and, if so, the amount of albuterol which passed through the mouse skin. These experiments were repeated several times using both single-layer (n=3) and double-layer (n=6) transdermal albuterol patches of the invention, prepared as described in Examples 2 and 3, respectively.

An eight week old male hairless mouse (Nu/Nu CD-1, Charles River, Bloomington, Mass.) was sacrificed by spinal dislocation, and then a rectangular piece of abdominal skin tissue was carefully lifted from the mouse and separated from the adhering fatty tissue and visceral material.

The abdominal skin tissue was then mounted on a Franz Diffusion Cell Assembly (Vanguard International, Neptune, N.J.) and clamped between the donor and receptor compartments thereof, with the epithelium portion of the skin tissue facing the donor compartment.

The temperature of the receptor compartment of the Franz Diffusion Cell Assembly was maintained by an external constant temperature water bath set at 37° C. A receptor solution (7 mL of normal saline solution) present in the receptor compartment was stirred with a magnetic stirrer to bath the dermis of the mouse skin tissue, thereby removing the adhering cell debris.

After two hours of this bathing, the receptor solution was withdrawn and replaced with 7 mL of fresh saline solution, which had been previously equilibrated at 37°. C.

Following this, an approximately 1.38 square centimeter transdermal patch of the invention, prepared as described in Example 2 (single-layer) or 3 (double-layer), was applied to the epidermal side of the mouse skin tissue, which was facing the donor compartment of the Franz Diffusion Cell Assembly, and the foil was removed from the patch.

After a period of 24 hours, a 300 microliter sample of the receptor solution was then removed from the sampling port of the apparatus and filtered. The albuterol concentration of the receptor solution sample was then determined by the High Performance Liquid Chromatography Method (HPLC) described below.

The HPLC system consisted of a 25 cm×4.6 mm Zorbax CN column (Zorbax, Dupont, Wilmington, Del.) and a mobile phase consisting of 5% acetonitrile and 95% water with 0.005 M pentane sulfonic acid, pH 2.5, low UV (v/v). The column temperature was ambient, and the mobile phase was pumped at a flow rate of 1.0 mL/minute. The detector was a Kratos SF 770 detector (Kratos Analytical Instruments, Ramsey, N.J.). Other parameters were as follows: chart speed, 0.5 cm/minute; wavelength, 200 nm; sensitivity, 0.6 AUFS; run time, 10 minutes; and injection volume, 40 $\mu$L.

The resulting chromatographic peak height was quantitated using the Ingrad Data Analysis System (G. D. Searle & Co., Skokie, Ill.), and compared with the standard calibration curve, to determine the unknown concentration of albuterol in the receptor solution sample. However, chromatographic peak heights may be calculated by other methods known by those of ordinary skill in the art.

The albuterol concentration obtained from the HPLC analysis was then converted into an amount (that amount of albuterol which was released from the transdermal albuterol patch in the donor compartment of the assembly and which passed across the mouse skin into the receptor solution contained in the receptor compartment of the assembly), by the following formula:

$$\text{amount of albuterol} = \text{concentration of albuterol (mg/mL)} \times \text{volume (7 mL)}$$

Once these experiments were performed three times each (n=3) for the single-layer, and six times each (n=6) for the double-layer, transdermal albuterol patches of the invention, the amounts were then normalized (adjusted to a 1 square centimeter patch by dividing the amount of albuterol calculated by the exact size of the patch actually cut) for the exposed surface area of the transdermal albuterol patch (approximately 1.38 square centimeters) to calculate the in vitro hairless mouse "skin permeation rate constant" (in vitro "release rate constant") (mg.cm$^{-2}$ day$^{-1}$).

The resulting "skin permeation rate constant" values obtained were then averaged separately for the single-layer (n=3) and double layer (n=6) patches to determine the mean (average) "skin permeation rate constant." These values are presented in Table I.

The mean hairless mouse "skin permeation rate constant" indicates the average amount of albuterol (in milligrams) which was released from a 1 square centimeter transdermal albuterol patch across a 1 square centimeter portion of skin of a hairless mouse during a period of twenty-four hours (mq.cm$^{-2}$.day$^{-1}$). It is a transdermal drug delivery patch parameter which is a characterization of the particular patch, and which can be compared to the same parameter of other transdermal patches to compare the ability of the various patches to deliver a particular active agent.

Skin permeation of albuterol incorporated into the patches was a function of the dissolution of albuterol in the Dow X7-3058 Silastomer TM elastomeric matrix material, and albuterol solubility and diffusivity in the hairless mouse skin membranes, especially the stratum corneum.

(2) Albuterol Solutions (a) Different Adjuvant Agents

In order to determine the affect of various adjuvant agents [ethanol (EtOH), Azone, and isopropyl alcohol (IPA)] on the flux of albuterol through the skin of a hairless mouse, the same experiments described above in Example 1(a)(I) were conducted, with the exceptions that: (1) rather than applying a transdermal albuterol patch to the epidermal side of the mouse skin tissue, approximately 3 mL of an albuterol solution consisting of approximately 10 mg of albuterol per mL of normal saline solution (NEAT I) with or without 50 mg/mL of adjuvant agent was added to the donor compartment of the Franz Diffusion Cell Assembly; (2) a 300 microliter sample was removed from the receptor compartment of the assembly (and replaced with the equivalent volume of normal saline solution) periodically over a period of 2, 5, 7 and 24 hours; and (3) the amounts of albuterol calculated were corrected for the dilution factor (because the original volume of receptor solution (7 mL) was diluted every time an additional 300 microliters of normal saline solution was added) by methods known by those of skill in the art.

The results of these experiments are presented in FIG. 1, and show that ethanol was the most effective adjuvant agent tested.

(b) Different Hydrocarbon Alcohols

In order to determine the affect of various normal hydrocarbon alcohols [dodecanol, nonyl alcohol, hexanol, n-propanol, decanol, and ethanol (EtOH)] on the flux of albuterol through the skin of a hairless mouse, these experiments were conducted again, as described in Example 1(a)(2)(a), but using these different normal hydrocarbon alcohols.

The results of these experiments are presented in FIG. 2, and show that, generally, the effect of the alcohol on albuterol flux increases as the chain length of the alcohol increases.

Example 1(b)

In Vitro Dissolution Experiments

In these preliminary in vitro experiments, the in vitro drug release of single-layer (Example 2) and double-layer (Example 3) transdermal patch formulations of the invention were also monitored, but via the dissolution of albuterol from the patches in water.

An approximately 8 square centimeter albuterol transdermal patch, prepared as described in Example 2 (single-layer) or 3 (double-layer), was mounted on the L holder of a Hanson's Dissolution Test Apparatus Model 72 RL (Hanson Research, Northridge, Calif.). The holder of the apparatus was composed of a stainless steel rod fitted with a circular disc and a metal screw cap. The screw cap had a 4 square centimeter open circular area in the center which was exposed to a dissolution medium consisting of 300 mL of water at 37° C. being stirred at 50 rpm.

5 mL samples of the dissolution medium were removed from the sampling port of the apparatus at periodic time intervals following the mounting of the patch on the apparatus (2, 5, 7 and 24 hours) for a period of twenty-four hours. Each volume of sample removed was replaced with mL of water to keep the amount of dissolution medium constant.

The albuterol concentration of each of these 5 mL samples was then determined by the method similar to that described in Example 1(a).

The albuterol concentrations were then converted into amounts in the manner similar to that described in Example 1(a) and corrected for the dilution factor, which was the volume of the dissolution medium (300 mL), also in the manner described in Example 1(a).

Once these experiments were performed three times each (n=3) for the single-layer, and six times each (n=6) for the double-layer, transdermal albuterol patches, the amounts calculated for those samples of dissolution medium removed from the Hanson's apparatus after 24 hours were normalized in the manner described in Example 1(a)(l) for the exposed surface area of the albuterol patches (approximately 4 square centimeters) to calculate the in vitro "dissolution rate constant" (mg.cm$^{-2}$.day$^{-1}$).

The resulting "dissolution rate constant" values obtained were then averaged separately for the single-layer (n=3) and double-layer (n=6) patches to determine the mean "dissolution rate constant." These values are presented in Table II.

The "dissolution rate constant" indicates the average amount of albuterol (in milligrams) which was released from a 1 square centimeter transdermal albuterol patch into the dissolution medium during a period of twenty-four hours (mg.cm$^{-2}$.day$^{-1}$). This is also transdermal drug delivery patch parameter which is a characterization of the particular patch, and which can be compared to the same parameter of other transdermal patches to compare the ability of the various patches to deliver a particular active agent. It is also used to predict the amount of active agent which will be released from a 1 square centimeter patch into the serum of a patient during a twenty-four hour period, and should correlate with the data obtained from in vivo experiments employing the same patches.

The time course of albuterol concentrations following patch dissolution in the Hanson's Dissolution Test Apparatus is shown in FIG. 3. This plot of drug release versus time was nonlinear and biphasic, showing a burst effect (rapid drug depletion in the initial phase). The magnitude of the burst effect was higher in the single-layer than in the double-layer patch. However, the amount of albuterol dissolved in the dissolution medium at 24 hours was similar in both patches (Table II).

Dissolution of albuterol from the patches into the dissolution medium was a function of the solubility of the drug, its diffusivity in the Dow X7-3058 Silastomer ™ elastomeric matrix material, the solubility and diffusivity of albuterol in water, and the resistance of the aqueous diffusion layer of the patches.

Example 1(c)

In Vitro Patch Residue Analysis Experiments

In these experiments, the albuterol release of single-layer (Example 2) (n=4) and double-layer (Example 3) (n=3) transdermal patch formulations of the invention were monitored via the permeation of albuterol from the patches through Rhesus monkey skin to determine whether or not albuterol would pass from the patch formulations through the monkey skin and, if so, the amount of albuterol which passed through the monkey skin.

After overnight fasting, each of Rhesus monkeys #388, #391, #423 and #430 was restrained in a chair, and then its chest area was clipped to remove hair. Chest skin surfaces were then wiped clean with an isopropyl alcohol solution.

An approximately 4 square centimeter transdermal patch of the invention, prepared as described in Example 2 (single-layer) or 3 (double-layer) was then applied to the chest area of each Rhesus monkey in the manner described in Example 1(a), pressing gently for proper adhesion. (While single-layer patches were applied to each of the four monkeys, double-layer patches were only applied to Rhesus monkeys #388, #391 and #423. Only one patch was applied to a monkey per experiment.)

The initial albuterol content in each patch had been estimated from the weight of the patch, the "content uniformity" (a value obtained by determining the average amount of albuterol extracted from similar-sized patches in the manner described below), and the "percent loading" (the percent of albuterol initially incorporated into the patch).

After 24 hours, the transdermal patch was carefully removed from each monkey, and then separated from its adhesive backing.

The residual content of albuterol in each patch was then determined by extracting the patch with 30 mL of acetone for a period of twenty-four hours, and then analyzing the extracts by the HPLC method described above in Example 1(a). From the initial and residual albuterol content in the patch, the loss of albuterol from the patch (absorbed amount) and, hence, the Rhesus monkey "skin permeation rate constant" (in vitro "release rate constant" of albuterol from the patch) in milligrams per square centimeter per day ($mg \cdot cm^{-2} \cdot day^{-1}$) was calculated in the following manner:

$$\text{Rhesus Monkey Skin Permeation Constant } (mg \cdot cm^{-2} \cdot day^{-1}) = \text{In Vitro Release Rate of Albuterol } (mg \cdot cm^{-2} \cdot day^{-1})$$

$$\text{Amount of Albuterol Absorbed } (mg \cdot cm^{-2} \cdot day^{-1}) = \text{Loss of Albuterol From the Patch } (mg \cdot cm^{-2} \cdot day^{-1}) =$$

$$\text{Initial Amount of Albuterol in the Patch } (mg \cdot cm^{-2}) - \text{Residual Amount of Albuterol In the Patch } (mg \cdot cm^{-2})$$

The mean values and standard deviations are presented in Table III.

In conclusion of Examples 1(a)–(c), the amount of albuterol released from the patches of the invention was dependent on the in vitro technique used, and decreased in the following manner: pad dissolution > monkey skin permeation > hairless mouse skin permeation. The in vitro "dissolution rates" from the patches (Example 1(b) and Table II) were faster than the "skin permeation rates" in hairless mouse (Example 1(a) and Table I) and Rhesus monkey (Example 1(c) and Table III). The hairless mouse "skin permeation rates" were somewhat lower, but comparable to the Rhesus monkey "skin permeation rates."

As shown in Tables I and II, the "dissolution rates" and hairless mouse "skin permeation rates" of the single-layer and double-layer albuterol patches were similar. However, as shown in Table III, the value of the Rhesus monkey "skin permeation rate constant" for a double-layer patch was higher than that for a single-layer patch.

In the double-layer patch experiment, albuterol content was monitored only in the layer of the patch which contained albuterol. It was not monitored in the layer which contained other formulation components. It is suspected that albuterol had migrated into the n-dodecanol layer, as it did into the skin membrane, thereby depleting the drug layer at a faster rate.

Example 1 (d)

"Intravenous Administration" of Albuterol to Rhesus Monkeys

Rhesus monkeys #388, #391, #423, and #430 were employed in a "crossover design" for the albuterol intravenous administration and transdermal patch administration bioavailability experiments described in Examples 1(d)–(f).

From each monkey, a 7 mL blood sample was removed on the day previous to the day of the albuterol intravenous administration bioavailability experiment, and then centrifuged to obtain the serum. The serum was then stored at −20° C. until the analysis described in Example 1(f)(1) was performed. These serum samples were used to make blanks and standards (controls).

Following this, the monkeys were fasted overnight, restrained and settled in chairs before receiving an intravenous injection of albuterol.

An albuterol solution containing 50 mcg of albuterol per mL of 0.9% sodium chloride was prepared. This solution was injected into the saphenous vein of each monkey at a dose of 1 mL/Kg of bodyweight.

A 5 mL blood sample was then taken from each monkey at 0.00, 0.08, 0.17, 0.33, 0.75, 1.00, 1.5, 2.00, 3.00, 4.00, and 5.00 hours following the albuterol injection. The serum from each blood sample was separated from other blood components via centrifugation, and then stored at −20° C. until the analysis described in Example 1(f)(1) was performed.

Example 1(e)

"Transdermal Patch Administration" of Albuterol to Rhesus Monkeys

After overnight fasting, on the day of the albuterol transdermal patch administration for the bioavailability experiment, the same four Rhesus monkeys described in Example 1(d) above (#388, #391, #423 and #430) were restrained in chairs, and then their chest areas were clipped to remove hair, avoiding any injury to the skin tissue. Chest skin surfaces were wiped with an isopropyl alcohol swab, and then an approximately 4 square centimeter albuterol transdermal patch of the invention, prepared as described in Example 2 (single-layer) or 3 (double-layer), was applied to the chest area of each monkey in the manner described in Example 1(a) for a period of 24 hours, after which it was removed in the manner described in Example 1(c). (While single-layer patches were applied to each of the four monkeys, double-layer patches were only applied to Rhesus monkeys #388, #391 and #423. Only one patch was applied to a monkey per experiment.)

A 5 mL blood sample was taken from each monkey at 0.00, 0.5, 1.00, 1.50, 3.00, 5.00, 7.00, 12.00, 24.00, 31.00, and 48.00 hours post transdermal albuterol patch application, centrifuged to obtain the serum, and then stored at −20° C. until the analysis described in Example 1(f)(2) was performed.

Monkey skin irritation was evaluated 24 hours post patch application by a Draize Score technique, as described by J. H. Draize, *Assoc. Food Drug Off.*, 46–47 (1959). The maximum possible score in this test is 4, indicating maximum skin irritation.

The scores obtained from this modified Draize Score technique were 0 or 1 for each of the four monkeys tested, indicating little or no skin irritation from the transdermal albuterol patches of the invention.

Moreover, no adverse skin reactions or sensitizations were seen when the monkeys were monitored for 7 days post patch application.

Example 1 (f)

Analysis of Serum Samples from the Albuterol "Intravenous Administration" and "Transdermal Patch Administration" Experiments Serum albuterol and bamethane sulphate, which was employed as an internal standard, were extracted from each of the serum samples described in Examples 1(d) and (e) into chloroform to remove polar interfering substances, and were then reextracted into the aqueous phase of the initial extraction to eliminate nonpolar materials, in the manner described directly below.

In separate clean test tubes, 1.5 mL of serum standard (Example 1(d)), serum sample (Examples 1(d) and (e)) and blank (Example 1(d)) was separately buffered with 150 microliters of a 0.42 M phosphate buffer, pH 7.2.

Each serum sample was then extracted with 4.5 mL of chloroform containing 0.1 M Di (2-ethylhexyl) phosphate (DEHP). The chloroform layer was separated into clean screw cap test tubes and mixed with 375 microliters of a 0.5 M HCl solution.

The aqueous extracts were then separated by centrifugation and analyzed by the HPLC-Fluorescence procedure described directly below.

The HPLC system consisted of a Waters Model 590 (Millipore Corporation, Bedford, Mass.) solvent delivery system equipped with a Waters Model 710 B Wisp auto injector, a Zorbax CN column (Dupont, 6 micron particles, 25 cm×4.6 mm internal diameter), Kratos (Kratos Analytical Instruments) Model 970 fluorescence detector (excitation 225 nm and emission 280 nm), and the Ingrad Data Analysis system (G. D. Searle & Co.). The mobile phase consisted of a mixture of 6 parts methanol in 94 parts aqueous solution of 0.005 M pentane sulfonic acid (pH 2.5). The mobile phase was pumped at a flow rate of 1.0 mL/minute. The injection volume was 100 microliters. The sensitivity of the method was 2.0 ng/mL.

The resulting chromatographic peak heights were quantitated using the Ingrad Data Analysis system, and compared with the standard calibration curve, to determine the unknown concentration of albuterol in each of the serum samples. However, chromatographic peak heights may be calculated by other methods known by those of ordinary skill in the art.

The standard calibration curve was linear over the concentration range of 2.5 to 200 ng/mL, as evidenced by the correlation coefficient of better than 0.99. The coefficient of variation associated with low (10 ng/mL) and high (80 ng/mL) quality control standard solutions were 4.5 and 3.4 percent, respectively.

Pharmacokinetic parameters were then estimated as described directly below, by conventional pharmacokinetic methods well known to those of ordinary skill in the art, and described by M. Gibaldi et al., Pharmacokinetics (New York 1975).

(1) Data Analysis of Serum Concentration Versus Time Profiles after "Intravenous Administration" of Albuterol Serum albuterol concentration time data obtained after albuterol "intravenous administration" are presented in Table IV, and were fitted to a two-compartment open model using 'C strip' and 'Nonlin' statistical computer programs, as described by J. G. Wagner, *J. Pharm. Sci.* 65, 1006–1010 (1976) and C. M. Metzler, *Research Biostatistics*, The Upjohn Co., Kalamazoo, Mich. (1974).

Model parameters were calculated using conventional pharmacokinetic equations, as described by M. Gibaldi et al., supra.

As can be seen in Table IV and FIG. 4, albuterol concentrations after "intravenous administration" declined biexponentially. (The initial portion of each of the curves in FIG. 4 was attributed to the distribution of albuterol to different tissues, and the terminal portion of the curves was attributed to the removal of albuterol via elimination processes.)

The mean pharmacokinetic parameters obtained via the 'Nonlin' program are shown in Table VI. The mean "initial half life" (the amount of time it took for 50% of the albuterol to get distributed into different body compartments) obtained was 6.0 minutes. The mean "terminal half-life" (the amount of time it took for 50% of the albuterol to be eliminated from the body), "clearance" (Cl) [rate of elimination of albuterol from the body (in milliliters of "apparent volume of distribution" per minute per kilogram of body weight (mL.minute$^{-1}$Kg$^{-1}$)), as described by M. Gibaldi et al., supra.], and "apparent volume of distribution" (a measure which indicates the extent of the distribution of albuterol in the body) obtained from the serum concentration time data (Table IV and FIG. 4) following the 50 mcg/mL intravenous injection of albuterol were 135.6±26.93 minutes, $10.2 \pm 1.8$ mL.minute$^{-1}$.Kg$^{-1}$, and $1935.9 \pm 37.2$ mL.Kg$^{-1}$, respectively.

The mean "terminal half-life" in monkeys is comparable to that in man, which ranges from 3 to 6 hours (from 180 to 360 minutes). The "clearance" value in monkeys agrees reasonably well with the previously-reported values of 6-8 mL.minute$^{-1}$.Kg$^{-1}$ in humans. Moreover, the "apparent volume of distribution" in humans is 2200 mL.Kg$^{-1}$, which is similar to that in monkeys.

In summary, the pharmacokinetic parameters determined for the Rhesus monkeys are similar to those reported for humans.

(2) Serum Analysis after "Transdermal Patch Administration" of Albuterol

The serum albuterol concentration time data obtained after the single-layer (Example 2) and double-layer (Example 3) albuterol transdermal patch application described in Example 1(e) to the four Rhesus monkeys is presented in Table V (single-layer) and Table XII (double-layer), and in FIG. 4.

Pharmacokinetic parameters were then estimated in the manner described directly below, and the mean values are presented in Table VII.

Following patch application, there was lag time ($t_L$) of approximately 3 hours before albuterol concentrations could be detected in the serum (FIG. 4). The time course release of albuterol administered transdermally through a patch of the invention showed a steady incline in each of the four monkeys tested up to 12 hours following the patch application. Thereafter, the "steady-state" serum albuterol concentrations ($C_{ss}$) (the concentration of albuterol remaining essentially the same over time, so that a plot of time versus albuterol concentration would show a horizontal plateau, due to the equilibrium reached between the rate of albuterol absorption and the rate of albuterol elimination from the body) were maintained until the transdermal patch was removed at 24 hours. As shown in FIG. 4 and Tables V and XII, serum drug levels were sustained for the 24-hour period, reaching steady state sometime between 12 and 24 hours. In all of the monkeys tested, albuterol concentrations declined rapidly after the patch was removed, with no measurable albuterol concentration remaining at 48 hours.

The albuterol "steady-state concentrations" (Css) in nanograms of albuterol per mL of serum (ng.mL$^{-1}$) after transdermal patch administration were calculated by averaging the mean 12- and 24-hour drug concentrations in serum.

In vivo "absorption rate constants" ($K_O$) in milligrams of albuterol absorbed from a 1 square centimeter patch over a period of twenty-four hours (mg.cm$^{-2}$ day$^{-1}$) were then calculated assuming an intravenous infusion-like input and using the formula:

$$[K_O = C_{ss} \cdot Cl]$$

where Cl is the "clearance" (rate of elimination of the drug from the body), and is calculated in the manner described by M. Gibaldi et al., supra. These values are presented in Table VII.

"Area under the curve" (AUC) values [values of the amount of albuterol in the serum at a given point in time (ng.mL$^{-1}$.hours)] were then calculated using the standard trapezoidal rule and the following mathematical formula, as described by M. Gibaldi et al. at Page 447:

$$\text{Area Under the Curve} \atop (AUC) = \frac{(C_1 + C_2)}{2} \times (t_2 - t_1)$$

where $C_1$ represents the first concentration, $C_2$ represents the second concentration, $T_1$ represents the first time and $t_2$ represents the second time, as shown in FIG. 5.

The resulting AUC values were then used to calculate the "bioavailability" (F) of albuterol administered transdermally through a single-layer or double-layer patch of the invention. These values are presented in Table VII.

The "skin bioavailability" (F) of albuterol administered transdermally through a single-layer or double-layer transdermal patch was calculated using the following mathematical equation, and using the dose and area under the curve (AUC) values obtained following the intravenous or transdermal administration of albuterol which are presented in Table XI:

$$\text{Skin Bioavailability} \atop (F) = \frac{AUC_{TR}}{AUC_{IV}} \times \frac{DOSE_{IV}}{DOSE_{TR}}$$

where, TR and IV represent transdermal and intravenous administration, respectively, and Dose represents the dose of albuterol given to the Rhesus monkey, either intravenously (50 mcg of albuterol per Kg of body weight) or transdermally. The "transdermal dose" was determined from the Rhesus monkey "skin permeation rate constant" ("in vitro release rate constant") presented in Table III. [The "transdermal dose" is equal to the Rhesus monkey "skin permeation rate constant" ("in vitro release rate constant")].

The "skin bioavailability" (F) of single-layer patches was calculated to be $115.0 \pm 16$ percent (Table VII). (The "skin bioavailability" (F) of the double-layer patches was not calculated.) This shows that, unlike the oral administration of albuterol, albuterol administered transdermally through a patch of the invention did not undergo a substantial first pass metabolism, and was 100% bioavailable. In addition, the patches maintained sustained serum drug levels of albuterol for a 24-hour period, with insignificant skin irritation.

The in vivo "absorption rate constant" calculated for the double-layer patch was higher than that calculated for the single-layer patch (Table VII). However, this difference was statistically insignificant [$p < 0.05$, based on the student's t-test (a statistical test employed to determine the difference between 2 means, which is known by those of skill in the art)].

The single-layer and double-layer transdermal albuterol patch formulations were bioequivalent in that their "steady-state concentration" ($C_{ss}$), in vivo "absorption rate constant" ($K_O$) and "area under the curve" (AUC) values (Table VII) were not statistically different ($p < 0.05$, based on the student's t-test).

(3) Comparison of In Vitro and In Vivo Data

A summary of the in vitro parameters of the albuterol patches of the invention is presented in Table IX. The hairless mouse "skin permeation rate constants," in vitro "dissolution rate constants" and Rhesus monkey "skin permeation rate constants" were obtained from Tables I, II and III, respectively.

The in vitro Rhesus monkey "skin permeation rate constants" (in vitro "release rate constants") determined in Example l(c) (Table III) were then compared with the in vivo Rhesus monkey "absorption rate constants" ($K_O$) calculated in Example 1(f)(2) (Table VII) to determine whether or not the Rhesus monkey in vitro data correlated with the Rhesus monkey in vivo data. These numbers are presented in Table VIII.

As can be seen in Table VIII, the in vitro Rhesus monkey "skin permeation rate constant" shows approximately a 1:1 correlation with the corresponding Rhesus monkey in vivo "absorption rate constant."

(4) Hypothetical Human Serum Albuterol Concentrations

The transdermal albuterol dose calculated in Example I(f)(2) (Table XI) was extrapolated from a 5-Kg Rhesus monkey to a 70-Kg human to predict the human serum albuterol concentrations shown in Table X. Assuming that the "clearance" (Cl) and in vivo "absorption rate constants" ($K_O$) for albuterol administered transdermally to monkeys are the same as those for humans, these values were used to predict albuterol concentration in a hypothetical 70-Kg human.

As shown in Table X, hypothetical albuterol serum concentrations were in the range of 8-10 ng/mL following applications of an 8 square centimeter single- or double-layer transdermal albuterol patch. These values compare reasonably well with those (11.0 and 11.1 ng/mL) obtained from the four-times-a-day instant release (IR) (4 mg) and the two-times-a-day controlled release (CR) (8 mg) albuterol sulphate tablet formulations in humans, as reported by R. S. Sykes et al., *Biopharm Drug Dispo.*, 9, 551–556 (1988) and M. L. Powell et al., *J. Clin. Pharmacol.* 26, 643–646 (1986).

Moreover, due to the increased bioavailability associated with the transdermal albuterol patches of the invention (6 mg of albuterol permeated from an 8 square centimeter patch), equivalent serum concentrations can be achieved with transdermal albuterol patches containing albuterol amounts of approximately 40 percent of that of the oral dose [16 mg total from either an instant-release (IR) tablet (4 mg of albuterol 4 times per day) or a controlled-release (CR) tablet (8 mg of albuterol 2 times per day)].

In patients, the once-a-day application of a transdermal albuterol patch of the invention should provide a similar therapeutic effect. This would also reduce the "Cmax value" (the maximum concentration of albuterol in the serum during a given period of time) in the serum, thereby minimizing side effects.

Example 1(g)

Rabbit Skin Irritation Tests

Rabbit skin irritation experiments were conducted in order to assess the potential irritant and/or corrosive effects of the transdermal albuterol patches of the invention on the skin of rabbits. The rabbit was the system of choice because rabbits have been used historically for this type of study. Thus, the data generated from this study could be compared to that generated from rabbits for other topical preparations.

Six young adult New Zealand White Rabbits, designated #7658/Male, #7661/Male, #7708/Female, #7687/Female, #7689/Female and #7692/Male, were obtained from a SLS and USDA approved supplier. The animals were maintained under standard laboratory conditions adhering to AAALAC standards. Animals were acclimatized for a minimum of five days prior to dosing.

On the day prior to dosing, the fur was clipped from the dorsal area of the trunk of each rabbit, using a small animal clipper.

On the day of dosing, a transdermal albuterol patch of the invention, prepared as described in Example 4 (single-layer), was applied to a small area of the exposed skin on two of the rabbits, and held in place with nonirritating tape. A stockinette sleeve was placed over the trunk of the two rabbits and secured at both ends with tape to prevent the removal and ingestion of the patches.

The rabbits were observed for pharmacological signs of toxicity at one and three hours both post patch application and prior to patch removal (approximately 24 hours post patch application). Following the 24-hour exposure period, there were no significant signs of toxicity to the two rabbits. Thus, the remaining four rabbits were dosed with a test patch in a similar manner.

The test patch was also removed from these four rabbits at 24 hours post patch application. The rabbit test site on each of the six rabbits was examined for signs of erythema and edema at scoring intervals of 24 and 72 hours post patch removal according to the dermal irritation grading system presented in Table XIII. If there was no evidence of dermal irritation at the 72-hour scoring interval, the study was terminated. If dermal irritation persisted at any test site, the observation period was extended for the affected animals (scored on day 7). Animals requiring an extended observation period remained on test until the irritation was resolved or permanent injury was evident.

The 24-hour, 72-hour and 7-day erythema and edema scores obtained for the six rabbits according to the dermal irritation system presented in Table XIII are presented in Table XV.

The 24- and 72-hour erythema and edema scores for each of the six rabbits were then added together, and the resulting total was divided by 12 (2×6 rabbits) to yield the mean Primary Irritation Index (P.I.I.). The mean P.I.I. was calculated to be 2.83, and was classified according to the standard evaluation criteria presented in Table XIV.

Example 1(h)

Guinea Pig Skin Sensitization Tests

Guinea pig skin sensitization tests were conducted in order to assess the potential of the transdermal albuterol patches of the invention to elicit a delayed contact hypersensitivity response (adverse skin reaction) in guinea pigs after multiple, separate applications of the patches to the guinea pigs. The guinea pig was the system of choice because guinea pigs have been used historically for this type of a study. Thus, the data generated from this study could be compared to that generated from guinea pigs for other topical preparations.

All transdermal albuterol patches of the invention employed in these experiments were prepared in the manner described in Example 4 (single-layer), were circular in shape and were approximately 1 centimeter in diameter.

Twenty-seven male Harley derived guinea pigs were obtained from an SLS and USDA approved supplier. The guinea pigs were maintained under the standard laboratory conditions adhering to the AAALAC standards, and were acclimatized for a minimum of five days prior to dosing.

Two guinea pigs were assigned to "Dermal Dose Range Finding Studies." Fifteen guinea pigs were assigned to "Dermal Sensitization Induction Studies," followed by "Dermal Sensitization Challenge Studies," followed by "Dermal Sensitization Rechallenge Studies." Five control guinea pigs were assigned to the "Dermal Sensitization Challenge Studies," and five control guinea pigs were assigned to the "Dermal Sensitization Rechallenge Studies."

(1) Dermal Dose Range Finding Studies

On the day prior to the dosing, the hair was clipped from the dorsal trunk area of the two guinea pigs designated for this study using a small animal clipper.

On the following day, one transdermal albuterol patch was applied to the exposed skin of each animal. Following this, a sheet of rubber dental dam was pulled taut over the dorsal trunk of each animal to completely occlude the test site.

Approximately six hours after dosing, the dental dam and patches were removed from each animal. The test sites were wiped with gauze moistened with distilled water, and the animals were returned to their individual cages.

Approximately twenty hours later, residual hair was removed from the exposure site on each guinea pig using a commercial depilatory. The depilatory was applied directly to the test sites and surrounding skin on each animal. Within 15 minutes, the depilatory was removed using warm running water and the animals were blotted dry using paper towels. A minimum of two hours after depilation, the test sites were graded for irritation according to the following scale:

Scoring Method

0 = No Reaction
± = Slight, Patchy Erythema
1 = Slight, but Confluent or Moderate, Patchy Erythema
2 = Moderate Confluent Erythema
3 = Severe Erythema with or without Edema Results of the "Dermal Dose Range Finding Studies" are presented in Table XVI. Dermal reaction in the two guinea pigs was limited to 0 and ± Scores. Thus, the patches were acceptable for the subsequent studies.

(2) Dermal Sensitization Induction Studies

On the day prior to dosing, the hair was clipped from the left flank area of each of the fifteen guinea pigs designated for these experiments, using a small animal clipper.

On the following day, one transdermal albuterol patch was applied to the exposed skin of each animal. Following this, a sheet of rubber dental dam was pulled taut over the left flank area of each animal to completely occlude the test sites.

Approximately six hours after dosing, the dental dam and patches were removed from each animal. The test sites were wiped with gauze moistened with distilled water, and the animals were returned to their individual cages.

The induction procedure was repeated for each test animal three times per week, until a total of nine induction applications had been made.

Following each induction procedure, test sites were scored 24- and 48-hours postdose for dermal irritation using the scoring method described above.

Following the final induction procedure, the guinea pigs were left untreated for a period of 14 days.

Results of the "Dermal Sensitization Induction Studies" are presented in Table XVII. Dermal reaction in the guinea pigs was limited to 0 and ± scores.

(3) Dermal Sensitization Challenge Studies

On the day prior to the Dermal Sensitization Challenge Studies, the hair was clipped from the posterior left flank area of the fifteen test guinea pigs, and from the five control guinea pigs, designated for these experiments using a small animal clipper.

On the following day, one transdermal albuterol patch was applied to the exposed virgin skin of each animal. Following this, a sheet of rubber dental dam was pulled taut over the posterior left flank area of each animal to completely occlude the test sites.

Approximately six hours after dosing, the dental dam and patches were removed from each animal. The test sites were wiped with gauze moistened with distilled water and the animals were returned to their individual cages.

Approximately twenty hours later, residual hair was removed from the exposure site on each animal using the commercial depilatory described above. The depilatory was applied directly to the test sites and surrounding skin on each animal. Within 15 minutes the depilatory was removed using warm running water, and the animals were blotted dry using paper towels. A minimum of two hours after depilation, the test sites were graded for irritation according to the scoring method described above.

Results of the "Dermal Sensitization Challenge Studies" are presented in Table XVIII. Dermal reaction in the guinea pigs was limited to 0 and ± Scores. Dermal reaction in control animals was limited to 0 scores.

(4) Dermal Sensitization Rechallenge Studies

Dermal Sensitization Rechallenge Studies were not conducted, because they were determined not to be necessary.

From these experiments, it was concluded that the transdermal albuterol patches of the invention are not contact sensitizers (do not cause adverse skin reaction as a result of multiple separate applications of the patches) in guinea pigs.

Example 1(i)

Transdermal Albuterol Patch Stability Studies

Stability studies were conducted to study the degradation of the transdermal albuterol patches of the invention at different temperatures (30° C., 45° C. and 55° C.) over a period of time (20 and/or 12 weeks) and, thus, to estimate the shelf lives of these patches.

The content of albuterol in several transdermal albuterol patches of the invention, which were prepared in the manner described in Example 4 (single-layer), was analyzed over a period of several weeks (20 and 12) as a function of loss of albuterol from the patches over time, which was calculated in the manner described in Example 1(c).

(1) Stability Study at 30° C.

Transdermal albuterol patches of the invention were separately wrapped in aluminum foil, and then placed in a sachet which was lined with polyethylene. The sachet was placed in a 30° C. oven. At periodic intervals over a period of 20 weeks, sample patches were removed from the oven, and then removed from the sachet and the aluminum foils.

The patches were then analyzed by the HPLC procedure described in Example 1(a).

The results of these experiments showed a 95 to 100 percent recovery of albuterol from patch samples stored at 30° C. during the period of 20 weeks. Thus, the transdermal albuterol patches of the invention were stable at 30° C. for the 20-week period.

(2) Stability Studies at 45° C. and 55° C.

Further stability studies were conducted at 45° C. and 55° C. in the manner described directly above, with the exceptions that: (a) 45° C. and 55° C. controlled-temperature cabinets were used in place of the oven; (b) patch samples were analyzed over a 12-week period according to the schedule presented below, where "Patch Analysis" indicates that 3 patches were removed from the controlled-temperature cabinet at the corresponding time and analyzed; and (c) a different HPLC method was used.

| Time | 45° C. Experiments | 55° C. Experiments |
|---|---|---|
| 0 Weeks | Patch Analysis | Patch Analysis |
| 2 Weeks | — | Patch Analysis |
| 3 Weeks | Patch Analysis | — |
| 4 Weeks | — | — |
| 6 Weeks | Patch Analysis | Patch Analysis |
| 9 Weeks | Patch Analysis | — |
| 12 Weeks | Patch Analysis | Patch Analysis |

After the sample patches were removed from the 45° C. and 55° C. controlled-temperature cabinets, and then separated from the sachet and the aluminum foils, they were then subjected to HPLC analysis using the HPLC system described directly below.

This HPLC system consisted of an Altex Ultrasphere ODS, C18 (25 cm×4.6 mm i.d.) 5 micron column (Altex Corporation, CA), and a mobile phase consisting of 1% triethylamine (TEA) buffer:methanol:acetonitrile (89:7:4). The column temperature was ambient, and the mobile phase was pumped at a flow rate of 1.0 mL per minute. Other parameters were as follows: detection, UV 210 nm at 0.2 AUFS; run time, 45 minutes; injection volume, 100 mcL; and sample concentration, 40 mcg/mL.

Results of the individual stability studies (per cent recovery of albuterol from patch samples, determined in the manner described above, and in the manner described in Example 1(c)) are presented in Tables XX (stability studies at 45° C.) and XXI (stability studies at 55° C.).

The percent of albuterol remaining in each patch versus time data at 45° C. and 55° C. was then simultaneously fitted to a nonlinear curve-fitting SAS computer program, which is known by those of skilled in the art.

Following this, the values of k25° C., k45° C., k55° C. and Ea were estimated using the SAS computer program, where k is the "degradation rate constant" and Ea is the "activation energy." From the value of k25° C., shelf-like (T85%, time required to reach 85% of the original potency) was estimated using a nonlinear regression analysis and the statistical computer program.

The "degradation rate constant," "activation energy" and "shelf-life estimation" values are shown in Table XIX. It appears that the "degradation rate constant" at 55° C. is at least three times faster than that at 45° C., and at least 50 to 60 times faster than that at 25° C. The activation energy is approximately 25 KCal/mole.

It appears that the patches, when stored at 25° C. would maintain 85% of their original potency for 169-182 weeks according to the "Mean Prediction Method," a method known by those of skill in the art, and for 143-156 weeks according to the "One Sided 95% Lower Confidence Level Prediction Method" (95% LCLPM), a method also known by those of skill in the art. Moreover, according to 95% LCLPM, it is predicted that future lots of the patches, when stored at 25° C., would maintain 85% of their original potency for 143-156 weeks.

In conclusion, from the stability experiments described above, it was predicted that the transdermal albuterol patches of the invention would retain a potency of 85% at ambient temperature over a 2-year period.

TABLE I

In Vitro Hairless Mouse Skin Permeation Rate Constants
(In Vitro Release Rate Constants)

(1) Single-Layer Albuterol Transdermal Patch (Example 2)
Mean = 0.50 mg · cm$^{-2}$ · day$^{-1}$ (n = 3)
Standard Deviation = 0.02 mg · cm$^{-2}$ · day$^{-1}$ (2) Double-Layer Albuterol Transdermal Patch (Example 3)
Mean = 0.45 mg · cm$^{-2}$ · day$^{-1}$ (n = 6)
Standard Deviation = 0.05 mg · cm$^{-2}$ · day$^{-1}$

TABLE II

In Vitro Albuterol Transdermal Patch
Dissolution Rate Constants
(mg · cm$^{-2}$ · day$^{-1}$)

(1) Single-Layer Albuterol Transdermal Patch (Example 2)
Mean = 2.34 mg · cm$^{-2}$ · day$^{-1}$ (n = 3)
Standard Deviation = 0.14 mg · cm$^{-2}$ · day$^{-1}$ (2) Double-Layer Albuterol Transdermal Patch (Example 3)
Mean = 2.37 mg · cm$^{-2}$ · day$^{-1}$ (n = 6)
Standard Deviation = 0.25 mg · cm$^{-2}$ · day$^{-1}$

TABLE III

Transdermal Patch Analysis before and after
Application to the Skin of Four Rhesus Monkeys
(#388, #391, #423 and #430)
Amounts of Albuterol in Transdermal Patch

| | Mean | Standard Deviation |
|---|---|---|
| (1) Single-Layer Albuterol Transdermal Patch (Example 2) | | |
| (1) Initial Amount (mg · cm$^{-2}$) | 6.26 (n = 4) | 2.30 |
| (2) Residual Amount (mg · cm$^{-2}$) | 5.50 (n = 4) | 1.98 |
| (3) Rhesus Monkey Skin Permeation Rate Constant (In vitro Release Rate Constant) (mg · cm$^{-2}$ · day$^{-1}$) | 0.76 (n = 4) | 0.28 |
| (2) Double-Layer Albuterol Transdermal Patch (Example 3) | | |
| (1) Initial Amount (mg · cm$^{-2}$) | 5.56 (n = 3) | 1.30 |
| (2) Residual Amount (mg · cm$^{-2}$) | 3.60 (n = 3) | 0.82 |
| (3) Rhesus Monkey Skin Permeation Rate | 1.96 (n = 3) | 0.46 |

TABLE III-continued

Transdermal Patch Analysis before and after Application to the Skin of Four Rhesus Monkeys (#388, #391, #423 and #430)
Amounts of Albuterol in Transdermal Patch

| | Mean | Standard Deviation |
|---|---|---|
| Constant (In vitro Release Rate Constant) $(mg \cdot cm^{-2} \cdot day^{-1})$ | | |

TABLE IV

Serum Concentration Time Data following Intravenous Injection of 50 mcg/kg Albuterol in Rhesus Monkeys

| Time Hours | Monkey #388 | Monkey #391 | Monkey #423 | Monkey #430 | Average | Standard Deviation |
|---|---|---|---|---|---|---|
| 0.00 | 0.00 | 0.00 | 0.00 | 0.00 | | |
| 0.08 | 102.00 | 73.60 | 84.30 | 73.00 | 57.72 | 38.83 |
| 0.17 | 40.70 | 56.90 | 46.80 | 45.00 | 47.35 | 8.40 |
| 0.33 | 23.70 | 39.70 | 29.10 | 31.60 | 31.02 | 6.65 |
| 0.75 | 13.20 | 17.90 | 19.60 | 16.60 | 16.82 | 2.71 |
| 1.00 | 10.60 | 18.70 | 14.30 | 13.80 | 14.35 | 3.33 |
| 1.50 | 8.00 | 12.50 | 14.60 | 11.20 | 11.58 | 2.76 |
| 2.00 | 8.74 | 11.50 | 12.70 | 9.66 | 10.65 | 1.78 |
| 3.00 | 5.63 | 7.55 | 12.30 | 8.32 | 8.45 | 2.80 |
| 4.00 | 5.43 | 6.33 | 7.84 | 6.04 | 6.41 | 1.02 |
| 5.00 | 6.82 | 4.53 | 7.59 | 4.13 | 5.77 | 1.70 |

TABLE V

Serum Concentration Time Data following Transdermal Application of a Single-Layer Albuterol Patch in Rhesus Monkeys

| Time Hours | Monkey #388 | Monkey #391 | Monkey #423 | Monkey #430 | Average | Standard Deviation |
|---|---|---|---|---|---|---|
| 0.0 | 0.00 | 3.69 | 0.00 | 0.00 | | |
| 0.5 | 3.03 | 0.00 | 0.00 | 0.00 | | |
| 1.0 | 0.00 | 0.00 | 0.00 | 0.00 | | |
| 1.5 | 0.00 | 0.00 | 0.00 | 0.00 | | |
| 3.0 | 4.87 | 3.90 | 0.00 | 2.67 | 2.86 | 2.11 |
| 5.0 | 11.00 | 11.40 | 6.94 | 4.39 | 8.43 | 3.36 |
| 7.0 | 20.90 | 22.60 | 18.40 | 9.15 | 17.76 | 6.00 |
| 12.0 | 29.00 | 31.60 | 45.50 | 27.50 | 33.40 | 8.24 |
| 24.0 | 29.40 | 31.10 | 74.30 | 67.40 | 50.55 | 28.92 |
| 31.0 | 8.47 | 10.70 | 20.00 | 17.70 | 14.21 | 6.74 |
| 48.0 | 0.00 | 8.74 | 2.90 | 4.26 | | |

TABLE VI

Mean and Standard Deviation of Pharmacokinetic Parameters obtained after Intravenous Injection of a 50 mcg/Kg Albuterol Solution in Rhesus Monkeys

| Parameter | Mean (n = 4) | Standard Deviation |
|---|---|---|
| (1) Area Under the Curve (AUC) $(ng \cdot mL^{-1} \cdot hour^{-1})$ | 84.19 | 16.15 |
| (2) Initial Half-Life (minutes) | 6.0 | 3.4 |
| (3) Terminal Half-Life (minutes) | 135.6 | 26.93 |
| (4) Terminal Elimination Rate Constant $(minute^{-1})$ | 0.0053 | 0.00094 |
| (5) Apparent Volume of Distribution $(mL \cdot Kg^{-1})$ | 1935.9 | 37.2 |
| (6) Clearance (Cl) $(mL \cdot minute^{-1} \cdot Kg^{-1})$ | 10.2 | 1.8 |

TABLE VII

Mean and Standard Deviation of Pharmacokinetic Parameters obtained after Transdermal Application of an Albuterol Transdermal Patch in Four Rhesus Monkeys

| Parameter | Mean (n = 4) | Standard Deviation |
|---|---|---|
| (1) Single-Layer Albuterol Transdermal Patch (Example 2) | | |
| (1) Weight of the monkey (Kg) | 5.39 | 0.025 |
| (2) Area Under the Curve (AUC) $(ng \cdot mL^{-1} \cdot hrs)$ | 1070.6 | 394.10 |
| (3) Steady State Serum Albuterol Concentration $(C_{ss})$ (12-24 hrs) $(ng \cdot mL^{-1})$ | 42.0 | 14.45 |
| (4) Clearance (Cl) $(mL \cdot minute^{-1} \cdot Kg^{-1})$ | 10.2 | 1.8 |
| (5) In vivo Absorption Rate Constant $(K_0)$ $(mg \cdot cm^{-2} \cdot day^{-1})$ | 0.81 | 0.20 |
| (6) Skin Bioavailability (F) of Albuterol (per cent (%)) | 115 | 16 |
| Double-Layer Albuterol Transdermal Patch (Example 3) | | |
| (1) Weight of the Monkey (Kg) | 5.33 | 0.2 |
| (2) Area Under the Curve (AUC) $(ng \cdot mL^{-1} \cdot hrs)$ | 1500.80 | 191.47 |
| (3) Steady State Serum Albuterol Concentration $(C_{ss})$ (12-24 hrs) $(ng \cdot mL^{-1})$ | 57.9 | 2.16 |
| (4) Clearance (Cl) $(mL \cdot minute^{-1} \cdot Kg^{-1})$ | 9.78 | 1.99 |
| (5) In vivo Absorption Rate Constant $(K_0)$ | 1.09 | 0.23 |

TABLE VII-continued

Mean and Standard Deviation of Pharmacokinetic Parameters obtained after Transdermal Application of an Albuterol Transdermal Patch in Four Rhesus Monkeys

| Parameter | Mean (n = 4) | Standard Deviation |
|---|---|---|
| (6) Skin Bioavailability (F) of Albuterol (per cent (%)) $(mg \cdot cm^{-2} \cdot day^{-1})$ | NC* | NC* |

*NC — Not Calculated

TABLE VIII

Comparison of the In Vitro Rhesus Monkey Skin Permeation Rate Constant and the In-Vivo Rhesus Monkey Absorption Rate Constant ($K_0$) after the Application of a Transdermal Albuterol Patch to Rhesus Monkeys

| | Rhesus Monkey Skin Permeation Rate Constant (In Vitro Release Rate Constant) $(mg \cdot cm^{-2} \cdot day^{-1})$ | | In Vivo Rhesus Monkey Absorption Rate Constant ($K_0$) $(mg \cdot cm^{-2} \cdot day^{-1})$ | |
|---|---|---|---|---|
| | Mean | Standard Deviation | Mean | Standard Deviation |
| 1. Single-Layer Patch (n = 4) | 0.76 | 0.28 | .81 | 0.20 |
| 2. Double-Layer Patch (n = 3) | 1.96 | 0.46 | 1.09 | 0.23 |

TABLE IX

Comparison of In Vitro Parameters of Transdermal Albuterol Patches

| Parameter | Table | Mean | Standard Deviation |
|---|---|---|---|
| (1) Single-Layer Albuterol Transdermal Patch (Example 2) | | | |
| Hairless Mouse Skin Permeation Rate Constant $(mg \cdot cm^{-2} \cdot day^{-1})$ | Table I | 0.50 (n = 3) | 0.02 |
| Dissolution Rate Constant $(mg \cdot cm^{-2} \cdot day^{-1})$ | Table II | 2.34 (n = 3) | 0.14 |
| Rhesus Monkey Skin Permeation Rate Constant $(mg \cdot cm^{-2} \cdot day^{-1})$ | Table III | 0.76 (n = 4) | 0.28 |
| (2) Double-Layer Albuterol Transdermal Patch (Example 3) | | | |
| Hairless Mouse Skin Permeation Rate Constant $(mg \cdot cm^{-2} \cdot day^{-1})$ | Table I | 0.45 (n = 6) | 0.05 |
| Dissolution Rate Constant $(mg \cdot cm^{-2} \cdot day^{-1})$ | Table II | 2.37 (n = 3) | 0.25 |
| Rhesus Monkey Skin Permeation Rate Constant $(mg \cdot cm^{-2} \cdot day^{-1})$ | Table III | 1.96 (n = 3) | 0.46 |

TABLE XI

Dose Versus Area Under the Curve Comparison following Intravenous and Transdermal Patch Application of Albuterol in Rhesus Monkeys

| Parameter | Mean | Standard Deviation |
|---|---|---|
| (1) Intravenous* Dose $(mg \cdot Kg^{-1})$ (n = 4) | 0.05 | 0.0 |
| (2) Transdermal** Dose: Single-Layer Patch $(mg \cdot Kg^{-1})$ (n = 4) | 0.76 | 0.28 |
| (3) Transdermal Dose:** Double-Layer Patch $(mg \cdot Kg^{-1})$ (n = 3) | NC*** | NC*** |
| (4) Area Under the Curve (AUC) after Intravenous Administration $(ng \cdot mL^{-1} \cdot hour^{-1})$ (n = 4) | 84.19 | 16.15 |
| (5) Area Under the Curve (AUC) after Single-Layer Transdermal Patch Administration $(ng \cdot mL^{-1} \cdot hour^{-1})$ (n = 4) | 1070.6 | 394.1 |
| (6) Area Under the Curve (AUC) after Double-Layer Transdermal Patch Administration $(ng \cdot mL^{-1} \cdot hour^{-1})$ (n = 3) | 1500.80 | 191.47 |

*Amount of albuterol injected into each of the Rhesus monkeys.
**Calculated from the Rhesus monkey "skin permeation rate constants" ("in vitro release rate constants") in Table III.
***NC—Not Calculated

TABLE X

Comparison of Hypothetical Human Serum Albuterol Concentrations from Transdermal Albuterol Patches Versus Literature-Reported Concentrations of Albuterol Tablets in a 70 Kg Human Being
Serum Concentration of Various Albuterol Formulations

| Single-Layer Patch (every 24 hours) | | Double-Layer Patch (every 24 hours) | | Controlled-Release (CR) Table Formulation | Instant-Release (IR) Tablet Formulation* |
|---|---|---|---|---|---|
| Serum Concentration (mg/mL) | Patch Size (cm²) | Serum Concentration (mg/mL) | Patch Size (cm²) | (8 mg of albuterol every 12 hours) (ng/mL) | (4 mg of albuterol every 6 hours) (ng/mL) |
| 2–4 | 4 | 3–5 | 4 | 11.0 | 11.1 |
| 4–8 | 8* | 6–10 | 8* | | |
| 8–16 | 16 | 12–20 | 16 | | |

*Approximately 6 mg of albuterol permeated from an 8 square centimeter patch.

TABLE XII

Serum Concentration Time Data following Transdermal Application of a Double-Layer Albuterol Patch in Rhesus Monkeys

| Time Hours | Monkey #388 | Monkey #391 | Monkey #423 | Average | S.D. |
|---|---|---|---|---|---|
| 0.0 | 0.000 | 0.287 | 0.000 | | |
| 0.5 | 0.000 | 0.000 | 0.000 | | |
| 1.0 | 0.000 | 0.000 | 0.000 | | |
| 1.5 | 0.000 | 0.000 | 0.779 | 0.26 | 0.45 |
| 3.0 | 1.270 | 2.270 | 8.790 | 4.11 | 4.08 |
| 5.0 | 24.200 | 14.900 | 25.100 | 21.40 | 5.64 |
| 7.0 | 44.700 | 22.200 | 33.200 | 33.36 | 15.91 |
| 12.0 | 58.500 | 42.900 | 53.400 | 51.60 | 7.95 |
| 24.0 | 59.300 | 68.100 | 65.600 | 64.33 | 4.53 |
| 31.0 | 10.900 | 26.900 | 33.300 | 23.70 | 11.54 |
| 48.0 | 0.000 | 0.000 | 0.000 | 0.00 | 0.00 |

TABLE XIII

Rabbit Dermal Irritation Grading System

| | Value |
|---|---|
| A. Erythema | |
| (1) No erythema; | 0 |
| (2) Very slight erythema (barely perceptible); | 1 |
| (3) Well-defined erythema; | 2 |
| (4) Moderate to severe erythema; and | 3 |
| (5) Severe erythema (beet redness) to slight eschar formations (injuries in depth) | 4 |
| B. Edema | |
| (1) No edema; | 0 |
| (2) Very slight edema (barely perceptible); | 1 |
| (3) Slight edema (edges of area well defined by definite raising); | 2 |
| (4) Moderate edema (raised approximately 1 mm); and | 3 |
| (5) Severe edema (raised more than 1 mm extending beyond the area of exposure). | 4 |

TABLE XIV

Dermal Evaluation Criteria

| Primary Irritation Index* (P.I.I.) | Irritation Rating |
|---|---|
| 0.00 | Nonirritant |
| 0.01–0.49 | Negligible Irritant |
| 0.50–1.99 | Slight Irritant |
| 2.00–4.99 | Moderate Irritant |
| 5.00–8.00 | Strong Irritant |

*Mean Primary Irritation Index = 2.83  (n = 6)

TABLE XV

Scores Obtained From the Rabbit Skin Irritation Tests

| Parameter | Scoring Interval | 7658/M | 7661/M | 7708/F | 7687/F | 7689/F | 7692/F |
|---|---|---|---|---|---|---|---|
| A. Erythema | 24 hours | 2 | 2 | 2 | 1 | 2 | 2 |
| | 72 hours | 4* | 2 | 2 | 0 | 1 | 2 |
| | 7 days | 1** | 1** | 0 | — | 0 | 0 |
| B. Edema | 24 hours | 2 | 1 | 1 | 1 | 1 | 2 |
| | 72 hours | 1 | 1 | 0 | 0 | 1 | 1 |
| | 7 days | 0 | 0 | 0 | — | 0 | 0 |

*Blanching
**Desquamation

TABLE XVI

Data Obtained from the Guinea Pig Dermal Dose Range Finding Studies

| Animal | 24 Hour | 48 Hour |
|---|---|---|
| 4648/Male | ± | ± |
| 4649/Male | ± | 0 |

TABLE XVII

Data Obtained from the Guinea Pig Dermal Sensitization Induction Studies (n = 15)

| Induction # | 24-Hour Mean ± Standard Deviation | 48-Hour Mean ± Standard Deviation |
|---|---|---|
| 1 | 0.0 ± 0.0 | 0.0 ± 0.0 |
| 2 | 0.0 ± 0.0 | 0.0 ± 0.0 |
| 3 | 0.3 ± 0.1 | 0.0 ± 0.0 |
| 4 | 0.0 ± 0.0 | 0.0 ± 0.0 |
| 5 | 0.3 ± 0.1 | 0.0 ± 0.0 |
| 6 | 0.3 ± 0.1 | 0.0 ± 0.0 |
| 7 | 0.3 ± 0.1 | 0.0 ± 0.0 |
| 8 | 0.0 ± 0.0 | 0.0 ± 0.0 |
| 9 | 0.1 ± 0.2 | 0.0 ± 0.0 |

TABLE XVIII

Data Obtained from the Guinea Pig Dermal Sensitization Challenge Studies

| Animals | Dermal Score (Mean ± Standard Deviation) 24 Hour | 48 Hour |
|---|---|---|
| Test Guinea Pigs (n = 15) | 0.3 ± 0.3 | 0.1 ± 0.2 |
| Control Guinea Pigs (n = 5) | 0.0 ± 0.0 | 0.0 ± 0.0 |

TABLE XIX

Parameters Generated from Stability Studies

| Parameter | Value |
|---|---|
| (1) Degradation Rate Constant (k) at 25° C. (k25° C.) (1/week) | 0.00096 ± 0.00011 Mean Standard Deviation (n = 3) |
| (2) Degradation Rate Constant (k) at 45° C. (k45° C.) (1/week) | 0.01603 ± 0.00063 Mean Standard Deviation (n = 3) |
| (3) Degradation Rate Constant (k) at 55° C. (1/week) | 0.05759 ± 0.00096 Mean Standard Deviation (n = 3) |
| (4) Arrhenius Activation Energy (Ea) (kCal/mole) | 26.54 ± 0.74 Mean Standard Deviation (n = 3) |
| (5) Mean (n = 3) Prediction of Time Required to Reach 85% of the Original Potency (T85%) at 25° C. (Weeks) | 169–182 Weeks (Mean Prediction Method) 143–156 Weeks (One Sided 95% Lower Confidence Level Prediction Method) 143–156 Weeks (One Sided 95% Lower Confidence Level Prediction Method for Future Samples) |

TABLE XX

Stability Studies of Albuterol Transdermal Patches at 45° C.

| Time | | Recovery of Albuterol from Patch Sample (Percent) | Mean and Standard Deviation (n = 3) (Percent) |
|---|---|---|---|
| (1) | 0 Weeks | 99.77<br>101.00 | 100.39 ± 0.864 |
| (2) | 3 Weeks | 94.12<br>99.61<br>95.19 | 96.31 ± 2.91 |
| (3) | 6 Weeks | 90.18<br>89.74<br>90.88 | 90.27 ± 0.58 |
| (4) | 9 Weeks | 86.47<br>87.66<br>85.81 | 86.65 ± 0.94 |
| (5) | 12 Weeks | 82.82<br>81.94<br>84.43 | 83.06 ± 1.27 |

TABLE XXI

Stability Studies of Albuterol Transdermal Patches at 55° C.

| Time | | Recovery of Albuterol from Patch Sample (Percent) | Mean and Standard Deviation (n = 3) (Percent) |
|---|---|---|---|
| (1) | 0 Weeks | 99.77<br>101.00 | 100.39 ± 0.864 |
| (2) | 2 Weeks | 89.51<br>87.56<br>89.42 | 88.83 ± 1.10 |
| (3) | 6 Weeks | 73.21<br>67.11<br>73.67 | 71.33 ± 3.67 |
| (4) | 12 Weeks | 41.94<br>53.67<br>54.80 | 50.14 ± 7.12 |

In summary, the results of Experiments 1(a)–(i) conducted with the transdermal albuterol patches described in Examples 2 (single-layer), 4 (single-layer) and 3 (double-layer) below showed an in vivo - in vitro correlation, a 100% albuterol skin bioavailability, sustained serum drug concentrations for 24 hours upon a once-a-day patch application, ease of administration of the patches, little or no skin irritation at the patch application site in either Rhesus monkeys or rabbits and good stability over a 2-year shelf life. In addition, Experiment 1(h) showed that these patches are not contact sensitizers in quiena pigs.

EXAMPLE 2

Preparation of Single Layer Transdermal Patch 100 g of an albuterol patch formulation was prepared With 71.81 of Dow X7-3058 Silastomer TM elastomeric matrix material:Dow X7-3059 crosslinking agent (97.86:2.14), 15.98 g of nonmicronized albuterol, 9.99 g of n-dodecanol, 1.75 g of glycerol, 0.35 g of hexanol and 0.125 g of X7-3075 catalyst.

In a clean mortar, the catalyst was mixed with the matrix material and crosslinking agent in a geometric dilution.

In a separate clean mortar, a fine paste of albuterol, n-dodecanol, hexanol and glycerol was made by combining and mixing the above-described amounts of these transdermal patch components. One portion of the matrix material-crosslinking agent-catalyst blend was then mixed thoroughly with the albuterol paste. Following this, the remaining two portions of the matrix material-crosslinking agent-catalyst blend were mixed one at a time with the matrix material-crosslinking agent-catalyst blend-albuterol paste.

The resulting mass was passed through a triple roller mill to obtain a homogeneous mixture. (A homogeneous mixture of the mass may be obtained by any suitable method, or with the use of any suitable equipment, as known by those of skill in the art.)

The mixture was then placed between two sheets of mylar plastic film (3M Corporation, St. Paul, Minn.), and passed through twin aluminum rollers of a film casting apparatus built by Applicants to adjust the thickness of the mixture to 0.3 mm by manipulating the gap between the two rollers of the apparatus to 0.3 mm. (The thickness of the mixture can be adjusted by any conventional film casting apparatus or other suitable equipment, as known by those of skill in the art.)

The resulting spread was then cured in an oven at 80° C. for 25 minutes.

The cured film was then cut into several pieces (from 1 to 16 square centimeters), and each piece was then separately glued with 355 Medical Adhesive (Dow Corning, Inc.) onto a piece of aluminum foil of corresponding size. The surface of the foil not in contact with the film was then adhered to a piece of adhesive-lined foam backing (Fasson, Painvile, Ohio) of corresponding size with 355 Medical Adhesive.

EXAMPLE 3

Preparation of Double Layer Transdermal Patch

A double-layer formulation transdermal albuterol patch of the invention was made, having separate albuterol and dodecanol layers.

100 g of an albuterol transdermal patch layer was prepared as described below using 73.875 g of Dow X7-3058 Silastomer TM matrix material:Dow X7-3059 crosslinking agent (97.86:2.14), 20 g of nonmicronized albuterol, 5.0 g of glycerol, 1.0 g of hexanol and 0.125 g of Dow X7-3075 catalyst.

100 g of an n-dodecanol transdermal patch layer was separately prepared as described below using 89.875 g of Dow X7-3058 Silastomer TM matrix material:Dow X7-3059 crosslinking agent (97:86:2.14), 10 g of n-dodecanol and 0.125 g of catalyst.

For each layer, catalyst was first mixed with the matrix material and crosslinking agent in a geometric dilution in a clean mortar to form a matrix material-crosslinking agent-catalyst blend.

In a separate clean mortar, a fine paste of albuterol, hexanol and glycerol was made using the above-described amounts of these transdermal patch components. One portion of the first matrix material-catalyst blend was mixed thoroughly with the albuterol paste. Following this, the remaining two portions of the first matrix material-catalyst blend were mixed one at a time with the matrix material-crosslinking agent-catalyst blend-albuterol paste.

The n-dodecanol transdermal patch layer was prepared separately by mixing the n-dodecanol described above with the other matrix material-crosslinking agent-catalyst blend.

The resulting masses of the albuterol and n-dodecanol layers were separately processed as follows. Each mass was passed through the triple roller mill described in Example 2 to obtain a homogeneous mixture. Each mixture was then separately placed between two sheets of mylar plastic film, as described above in Example 2, and passed through two aluminum rollers of the film casting apparatus described in Example 2. Each resulting spread was then cured in an oven at 80° C. for 25 minutes.

The cured albuterol and n-dodecanol film layers were then cut into pieces, each measuring from 1 to 16 square centimeters. Each n-dodecanol layer was then placed upon an albuterol layer of corresponding size, and adhered naturally thereto.

The surface of the n-dodecanol layer not in contact with the albuterol layer was then glued to a piece of aluminum foil of corresponding size with 355 Medical Adhesive.

The surface of the foil not in contact with the n-dodecanol layer was then adhered to a piece of adhesive-lined foam backing (Fasson, supra.) of corresponding size with 355 Medical Adhesive.

EXAMPLE 4

Preparation of Single Layer Transdermal Patch
(Preferred Method of Preparation)

Using the same materials set forth in Example 2, with the exception of the substitution of micronized albuterol for nonmicronized albuterol, and the same quantities thereof, single-layer transdermal albuterol patches of the invention were prepared in the following manner.

In a clean mortar, the Dow X7-3058 Silastomer ™ elastomeric matrix material was mixed with X7-3059 crosslinking agent in the proportion of 97.86:2.14. This mixture was then aged for two days prior to use. (It should be aged for not less than 2, and not more than 7, days prior to use.)

In a separate clean container, the albuterol, n-dodecanol, glycerol, hexanol and catalyst were mixed with a spatula to make a fine paste.

Then, the matrix material-crosslinking agent blend was added to the other mixture and mixed thoroughly in a porcelain mortar with a pestle.

The resulting mixture was then passed twice through the triple roller mill described in Example 2.

An aliquot of the mixture was then transferred into a syringe which had had its tip cut. (The size of the aliquot is not critical, and may vary according to the size of the syringe employed.) The aliquot of the mixture was then placed between two sheets of mylar plastic film (3M Corporation) with the syringe.

From this point on, this experiment was conducted in the manner described in Example 2.

This method is preferable to the method described in Example 2 for preparing single-layer transdermal albuterol patches of the present invention.

Therapeutically-active agents which produce a systemic activity, and which are deliverable by the present invention are, for instance, and without limitation, anti-infectives, for example pentamidine and lomefloxacin, antibiotics, for example metronidazole, hormones, antipyretics, antidiabetics, coronary dilation agents, glycosides, spasmolytics, antihypertensives, for example verapamil and its enantiomers and betaxolol, psychoactive agents, for example zolpidem, cycloserine and milacemide, corticosteroids, analgesics, contraceptives, nonsteroidal anti-inflammatory drugs, for example oxaprozen, antioholinergics, sympatholytics, sympathomimetics, vasodilatory agents, anticoagulants, antiarrhythmics, for example disopyramide or disobutamide, and prostaglandins having various pharmacologic activities, for example misoprostol and enisoprost.

While the transdermal patches of the present invention have been described and illustrated herein some specifivity, and with reference to certain prepared embodiments thereof, those skilled in the art will appreciate that various changes, modifications and substitutions can be made therein without departing from the spirit and scope of the invention. For example, effective dosages of active agent other than the preferred ranges set forth hereinabove may be applicable as a consequence of variations in the responsiveness of the patient being treated, dosage-related adverse effects, if any, and analogous considerations. Likewise, the specific pharmacological responses observed may vary according to, and depending upon, the particular active compounds selected for incorporation into the patches. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A monolayer patch for the transdermal administration of albuterol comprising:
   a. an elastomeric matrix, said elastomeric matrix being present in an amount ranging from about 25 to about 85 per cent, weight to weight;
   b. albuterol, said albuterol being present in an amount ranging from about 2 to about 30 per cent, weight to weight; and
   c. a diffusion enhancer, said diffusion enhancer being a normal hydrocarbon alcohol having from about 1 to about 20 carbon atoms, and said diffusion enhancer being present in an amount ranging from about 3 to about 30 per cent, weight to weight;
   said patch having a thickness of between about 0.05 and about 0.5 millimeters, and said patch having an area which is in the range of from about 1 to about 100 square centimeters.

2. The patch according to claim 1 wherein said elastomeric matrix is present in an amount ranging from about 65 to about 90 per cent, weight to weight.

3. The patch according to claim 1 wherein said elastomeric matrix is a silicone elastomer.

4. The patch according to claim 1 wherein said diffusion enhancer is n-dodecanol.

5. The patch according to claim 2 wherein said diffusion enhancer is n-dodecanol.

6. The patch according to claim 5 said n-dodecanol is present in an amount ranging from about 6 to about 15 per cent, weight to weight.

7. The patch according to claim 6 wherein said albuterol is present in an amount ranging from about 8 to about 24 per cent, weight to weight.

8. The patch according to claim 7 wherein said albuterol is present in an amount ranging from about 12 to about 20 per cent, weight to weight.

9. The patch according to claim 3 wherein said diffusion enhancer is n-dodecanol.

10. The patch according to claim 1 wherein said diffusion enhancer is n-dodecanol.

11. The patch according to claim 1, additionally comprising a plasticizer.

12. The patch according to claim 11 said plasticizer is a polyol.

13. The patch according to claim 12 wherein said polyol is glycerol.

14. The patch according to claim 11, additionally comprising a solubilizer.

15. The patch according to claim 14 wherein said solubilizer is a normal hydrocarbon alcohol.

16. The patch according to claim 15 wherein said hydrocarbon alcohol is n-hexanol.

17. The patch according to claim 1, 2, 3, 4, 5, 6, 7, 8, 9, 10, 11, 12, 13 or 14, additionally comprising a curing catalyst for said elastomeric matrix.

18. The patch according to claim 17 additionally comprising a backing member.

19. The patch according to claim 18 additionally comprising a protective release film and/or a low adhesion back side coating.

20. A method of administering albuterol to a mammal in need thereof, comprising the step of administering to the skin or mucosal areas of said mammal a patch according to claim 1, 3, 4, 6, 9 or 10.

21. A method of treating bronchial constriction and/or urticaria in a mammal in need thereof, comprising the step of applying to the skin or mucosal areas of such animal a patch according to claim 1, 3, 4, 6, 9, or 10.

22. A method of delaying premature uterine contractions in a pregnant mammal in need thereof, comprising the step of applying to the skin or mucosal areas of said mammal a patch according to claim 1, 3, 4, 6, 9 or 10.

23. A double layer patch for the transdermal administration of albuterol comprising an albuterol layer and a diffusion enhancer layer, said albuterol layer comprising:
   a. an elastomeric matrix, said elastomeric matrix being present in an amount ranging from about 25 to about 95 per cent, weight to weight, and
   b. albuterol, said albuterol being present in an amount ranging from about 2 to about 30 per cent, weight to weight, and said diffusion enhancer layer comprising:
   a. an elastomeric matrix, said elastomeric matrix being present in an amount ranging from about 25 to about 95 per cent, weight to weight, and
   c. a diffusion enhancer, said diffusion enhancer being a normal hydrocarbon alcohol having from about 1 to about 20 carbon atoms, and said diffusion enhancer being present in an amount ranging from about 3 to about 30 per cent, weight to weight;

said patch having a thickness of between about 0.05 and about 0.5 millimeters, and said patch having an area which is in the range of from about 1 to about 100 square centimeters.

* * * * *

UNITED STATES PATENT AND TRADEMARK OFFICE
CERTIFICATE OF CORRECTION

PATENT NO. : 5,164,189

DATED : November 17, 1992

INVENTOR(S) : Farhadieh, et al.

It is certified that error appears in the above-identified patent and that said Letters Patent is hereby corrected as shown below:

Column 5, line 58, reading "I(b)" should read -- 1(b) --.

Column 6, line 4, reading "int eh" should read -- in the --.

Column 6, line 16, reading "$t_2$" should read -- $t_2$ represents the second time --.

Column 11, line 57, reading "(Example I)" should read -- (Example 1) --.

Column 14, line 34, reading "I.0" should read -- 1.0 --.

Column 16, line 19, reading "with mL" should read -- with 5 mL --.

Column 16, line 55, reading "from a I" should read -- from a 1 --.

Column 23, line 17, reading "I(f)(2)" should read -- 1(f)(2) --.

Column 27, line 47, reading "of I%" should read -- of 1% --.

Column 27, line 63, reading "of skilled" should read -- of skill --.

Column 28, line 1, reading "shelf-like" should read -- shelf life --.

Column 35, line 56, reading "With" should read -- with --.

UNITED STATES PATENT AND TRADEMARK OFFICE
CERTIFICATE OF CORRECTION

PATENT NO. : 5,164,189

DATED : November 17, 1992

INVENTOR(S) : Farhadieh, et al.

It is certified that error appears in the above-identified patent and that said Letters Patent is hereby corrected as shown below:

Column 35, line 58, reading "(97.86:2.I4)" should read -- (97.86:2.14) --.

Column 37, line 8, reading "1 to I6" should read -- 1 to 16 --.

Column 37, line 66, reading "antioholinergics" should read -- anticholinergics --.

Column 38, line 32, reading "to about 85" should read -- to about 95 --.

Column 38, line 54, reading "5 said" should read -- 5 wherein said --.

Column 39, line 1, reading "11 said" should read -- 11 wherein said --.

Signed and Sealed this

Twelfth Day of April, 1994

Attest:

BRUCE LEHMAN

*Commissioner of Patents and Trademarks*

*Attesting Officer*